(12) United States Patent
Osorio

(10) Patent No.: US 10,850,034 B2
(45) Date of Patent: Dec. 1, 2020

(54) AUTOMATIC TREATMENT OF PAIN

(71) Applicant: Ivan Osorio, Leawood, KS (US)

(72) Inventor: Ivan Osorio, Leawood, KS (US)

( * ) Notice: Subject to any disclaimer, the term of this patent is extended or adjusted under 35 U.S.C. 154(b) by 88 days.

(21) Appl. No.: 16/201,876

(22) Filed: Nov. 27, 2018

(65) Prior Publication Data

US 2019/0091403 A1 Mar. 28, 2019

Related U.S. Application Data

(63) Continuation-in-part of application No. 15/164,697, filed on May 25, 2016, now Pat. No. 10,232,114,
(Continued)

(51) Int. Cl.
*A61M 5/172* (2006.01)
*A61N 1/36* (2006.01)
(Continued)

(52) U.S. Cl.
CPC ......... *A61M 5/1723* (2013.01); *A61B 5/0205* (2013.01); *A61B 5/02055* (2013.01); *A61B 5/165* (2013.01); *A61B 5/4824* (2013.01); *A61B 5/4839* (2013.01); *A61N 1/025* (2013.01); *A61N 1/08* (2013.01); *A61N 1/36021* (2013.01); *A61N 5/0625* (2013.01); *G16H 10/60* (2018.01); *G16H 20/17* (2018.01); *G16H 40/63* (2018.01); *G16H 50/30* (2018.01); *G16H 50/70* (2018.01); *A61B 3/11* (2013.01); *A61B 5/021* (2013.01); *A61B 5/024* (2013.01); *A61B 5/02405* (2013.01); *A61B 5/053* (2013.01); *A61B 5/0533* (2013.01); *A61B 5/087* (2013.01); *A61B 5/0816* (2013.01); *A61B 5/1118* (2013.01); *A61B 5/14539* (2013.01); *A61B 5/14542* (2013.01); *A61B 5/14552* (2013.01); *A61B 5/42* (2013.01);
(Continued)

(58) Field of Classification Search
CPC ............ A61N 1/36071; A61N 1/36139; A61N 1/36021; A61N 1/36114; A61B 5/4824; A61B 5/0476; A61B 5/7275; A61K 45/06; A61K 31/485; A61M 5/1723; A61M 21/02
See application file for complete search history.

(56) References Cited

U.S. PATENT DOCUMENTS

2011/0137134 A1* 6/2011 Hemmerling ....... A61M 5/1723
600/301
2011/0251468 A1* 10/2011 Osorio ................... G16H 50/30
600/300

\* cited by examiner

*Primary Examiner* — Manuel A Mendez
(74) *Attorney, Agent, or Firm* — Rodney J. Fuller; Booth Udall Fuller, PLC

(57) ABSTRACT

Disclosed are methods and medical device systems for automated delivery of therapies for pain and determination of need for and safety of treatment. In one embodiment, such a medical device system may comprise a sensor configured to sense at least one body signal from a patient; and a medical device configured to receive a first sensed body signal from the sensor; determine a patient pain index based at least in part on said first sensed body signal; determine whether said patient pain index is above at least a first pain index threshold; determine a safety index based at least in part on a second sensed body signal; select a pain treatment regimen based on at least one of said safety index and or a determination that said pain index is above said first pain index threshold; and deliver said pain treatment regimen.

20 Claims, 12 Drawing Sheets

Related U.S. Application Data which is a continuation of application No. 13/836,974, filed on Mar. 15, 2013, now Pat. No. 9,579,457.

(60) Provisional application No. 62/590,943, filed on Nov. 27, 2017.

(51) Int. Cl.

| | |
|---|---|
| *A61B 5/16* | (2006.01) |
| *G16H 50/30* | (2018.01) |
| *G16H 10/60* | (2018.01) |
| *A61B 5/0205* | (2006.01) |
| *A61N 5/06* | (2006.01) |
| *A61N 1/02* | (2006.01) |
| *A61N 1/08* | (2006.01) |
| *G16H 20/17* | (2018.01) |
| *G16H 40/63* | (2018.01) |
| *G16H 50/70* | (2018.01) |
| *A61B 5/00* | (2006.01) |
| *A61B 3/11* | (2006.01) |
| *A61B 5/087* | (2006.01) |
| *A61M 5/14* | (2006.01) |
| *A61B 5/024* | (2006.01) |
| *A61N 5/067* | (2006.01) |
| *A61M 5/142* | (2006.01) |
| *A61B 5/021* | (2006.01) |
| *A61B 5/053* | (2006.01) |
| *A61B 5/1455* | (2006.01) |
| *A61B 5/11* | (2006.01) |
| *A61B 5/145* | (2006.01) |
| *A61B 5/08* | (2006.01) |

(52) U.S. Cl.
CPC ............. *A61B 5/483* (2013.01); *A61B 5/4803* (2013.01); *A61B 5/486* (2013.01); *A61B 5/4827* (2013.01); *A61B 5/4866* (2013.01); *A61B 2560/0242* (2013.01); *A61B 2562/0219* (2013.01); *A61M 5/14* (2013.01); *A61M 5/14244* (2013.01); *A61M 5/14276* (2013.01); *A61M 2005/1405* (2013.01); *A61M 2205/332* (2013.01); *A61M 2205/3306* (2013.01); *A61M 2205/3327* (2013.01); *A61M 2205/3569* (2013.01); *A61M 2205/3584* (2013.01); *A61M 2205/3592* (2013.01); *A61M 2205/50* (2013.01); *A61M 2205/52* (2013.01); *A61M 2205/8206* (2013.01); *A61M 2230/005* (2013.01); *A61M 2230/04* (2013.01); *A61M 2230/06* (2013.01); *A61M 2230/08* (2013.01); *A61M 2230/30* (2013.01); *A61M 2230/40* (2013.01); *A61M 2230/42* (2013.01); *A61M 2230/50* (2013.01); *A61M 2230/62* (2013.01); *A61M 2230/63* (2013.01); *A61N 2005/067* (2013.01)

AUTOMATIC TREATMENT OF PAIN

CROSS-REFERENCE TO RELATED APPLICATION

This application is a continuation-in-part of U.S. patent application Ser. No. 15/164,697, filed on May 25, 2016 (published as US 20160263318), which is a continuation of U.S. patent application Ser. No. 13/836,974, filed on Mar. 15, 2013 (now U.S. Pat. No. 9,579,4571); this application also claims the benefit of and priority to U.S. Provisional Application No. 62/590,943, filed on Nov. 27, 2017, the contents of each of which are incorporated herein by reference in their entireties for all purposes.

FIELD OF THE DISCLOSURE

This disclosure relates generally to medical device systems and, more particularly, to medical device systems and methods capable of automated delivery of treatments for pain.

DESCRIPTION OF THE RELATED ART

There have been many advances in the treatment of pain. In order to facilitate faster delivery of pain medication to a patient, healthcare providers have recently added a new dimension in delivering pain medication—machine delivery of medication. In addition to the manual delivery of pain medication under a patient's control, medication systems can now be connected to an intravenous (i.v.) delivery system that can deliver medication without manual intervention by a healthcare professional. For example, healthcare providers may employ a pain medication delivery device that is capable of delivering a predetermined dosage of pain medication in response to a patient's request. Some devices can operate under the control of a handheld unit, wherein when a patient depresses a button on a handheld unit, the pain medication device pumps a predetermined dosage of medication to the patient, intravenously.

Although state-of-the-art pain medication devices are capable of rapidly delivering medication to a patient, the delivery of these medications is generally based upon a predetermined schedule and dosage or on a patient's subjective pain scale. In some cases, the predetermine dosage may not be adequate, or maybe too high, resulting in inadequate pain relief, over-medication, or other health issues. Further, giving a patient full control of activating the delivery of medication may lead to over-usage of pain medication, which may have acute adverse effects such as cardio-respiratory depression, confusion or falls to the ground; addiction and chronic abuse of pain medications is also a common consequence of unregulated or careless administration of pain medications. Patients may self-medicate with pain medication for psychological or pleasurable effects, not to alleviate pain. It would be desirable to alleviate a patient's pain using methods and systems that: 1. Do not require intervention by medical practitioners or by the patient; 2. Deliver the dose necessary and sufficient to relieve the pain while reducing over-usage of pain medication; 3. The method and system of delivery is prophylactic, that is, it prevents or anticipates the emergence of painful sensations effectively breaking the pain cycle and its associated suffering/distress, thus decreasing the probability of development of chronic pain syndromes.

SUMMARY OF THE DISCLOSURE

In one embodiment, the present disclosure provides a medical device system, comprising at least one sensor configured to sense at least one body signal from a patient; and a medical device configured to receive at least a first sensed body signal from said at least one sensor; determine a patient pain index, wherein said patient pain index is based at least in part on said first sensed body signal; determine whether said patient pain index is above at least a first pain threshold; determine a safety index wherein said safety index is based at least in part on a second sensed body signal; select a pain treatment regimen based on at least one of said safety index or a determination that said pain index is above said first pain threshold; and deliver said pain treatment regimen.

In one embodiment, the present disclosure provides a method for providing pain medication, comprising receiving, at a device, a request for delivery of a pain medication to a patient; receiving, automatically by the device, at least one body data series of said patient in response to said request for delivery of a pain medication; determining a patient pain index based upon said body data series; determining whether the patient pain index is above a reference pain index; determining a safety index; and allowing, automatically, delivery of a pain medication based on at least one of said safety index or a determination that said patient pain index is above said reference pain index.

In one embodiment, the present disclosure provides a method for providing pain medication to a patient, comprising receiving automatically, at least a first body data series of a patient; determining a first discomfort index of the patient based upon said first body data series; determining whether the first discomfort index exceeds a first discomfort index threshold; and providing a first therapy in response to determining that said first discomfort index does not exceed said first discomfort index threshold.

In one embodiment, the present disclosure provides a method, comprising receiving at a device, a request for delivery of a pain therapy to a patient; receiving, automatically by the device, at least one body data series in response to said request for delivery of a pain therapy; determining a patient pain index based upon said body data series; determining whether the patient pain index is above a patient pain index threshold; and automatically delivering a pain therapy to the patient in response to determining that said patient pain index is above said patient pain index threshold.

In one embodiment, the present disclosure provides a method for providing pain medication, comprising receiving at least one of a request for delivery of a pain medication from a patient, an indication of an elapsed time period, or a request for administration of a responsiveness test to a patient; administering a responsiveness test to the patient in response to said receiving; and allowing delivery of a pain medication based on a determination that the patient's responsiveness is above a responsiveness threshold.

In one embodiment, the present disclosure provides a non-transitory computer readable program storage unit encoded with instructions that, when executed by a computer, perform a method referred to above.

Figure 1:
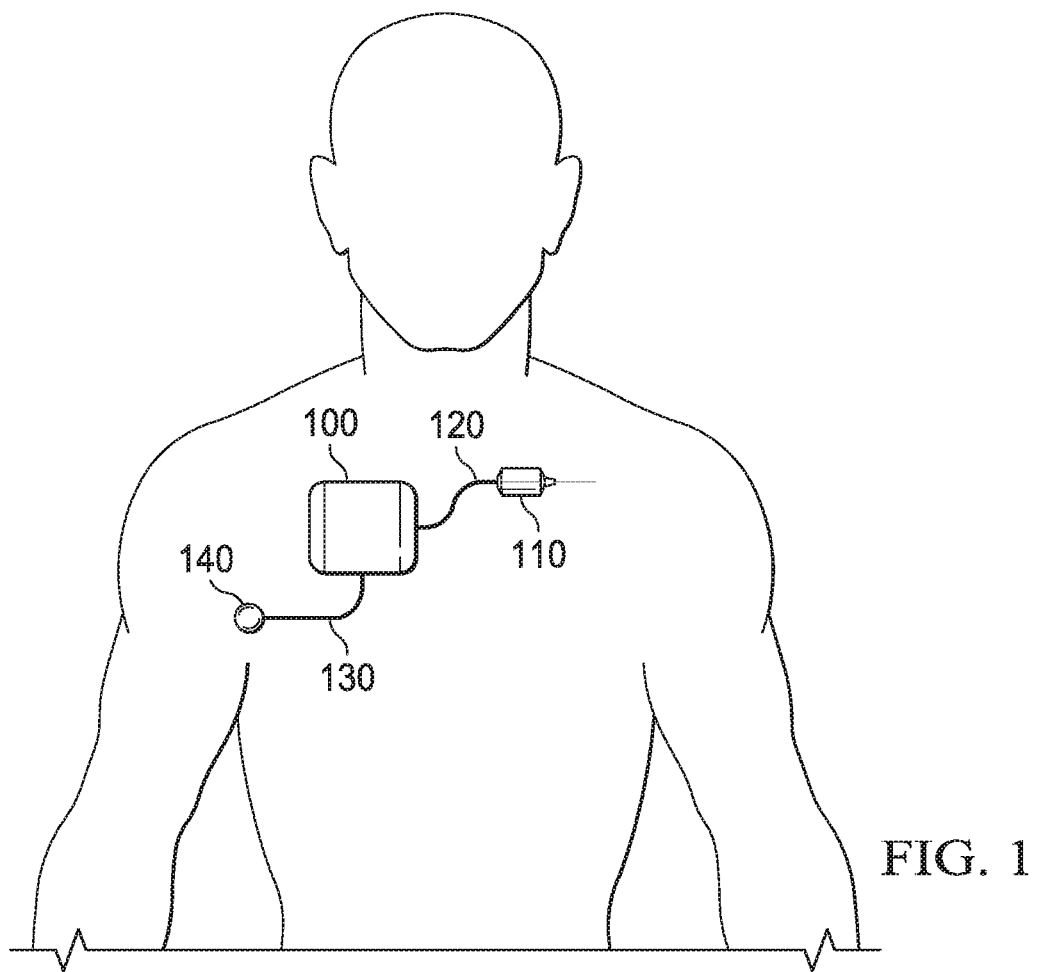
FIG. 1 illustrates a stylized depiction of a medication dispensing device, in accordance with one embodiment of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF THE SPECIFIC EMBODIMENTS

Embodiments of the present disclosure provide for a medical device for dispensing therapeutic treatment, such as pain medication. The medical device may be a standalone device that may be operatively coupled to a delivery mechanism (e.g., an i.v. infusion pump), which may be used to deliver treatment to the patient. In one embodiment, the medical device may include a portable device carried by the patient. In another embodiment, it may include an implantable device. The medical devices of embodiments of the present disclosure may include various capabilities for detecting one or more body signals (physiological or pathological) of the patient, analyzing these signals, using the results of analysis to assess the patient vital signs, neurological state, and the pain or suffering/distress level, and automatically deliver therapy or, if the system is in a manual operation mode, grant the request if, based on the analysis of the signals, therapy delivery is deemed both safe and necessary. In one embodiment, the medical device may be capable of forecasting pain or distress levels and prophylactically and automatically deliver medication, to prevent (conscious) pain perception or the suffering, distress and anxiety associated with the anticipation of pain. In this manner, delivery of medication is safe and timely with minimal or no interaction from the patient and is highly efficacious. The methods and systems described herein may reduce prevent or reduce pain while limiting over-usage of pain medication, thereby keeping the patient comfortable and reducing adverse effects of, or the potential for abusing pain medications.

Illustrative embodiments of the disclosure are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

One of the benefits of utilizing such an automated system includes the fact that prior to full onset of pain, delivery of analgesic, anesthetic or anxiolytic medications may take place, preventing onset of pain or, at a minimum, providing immediate relief In order to achieve this, certain physiological signals or indices derived from such signals may be recorded and analyzed in order to anticipate onset of pain or quantify it if already present. If delivery of pain medication is contingent upon perception of pain by the patient, a "pain cycle" may be established. "Pain cycles" facilitate in certain patients chronic pain syndromes, a serious complication due to its detrimental effects on a patient's health, productivity and quality of life. Automated systems provided by embodiments herein may reduce or even substantially prevent the emergence of "pain cycles."

Moreover, in other embodiments of the present disclosure, a request by the patient for pain medication may prompt a physiological evaluation of the patient to be made in order to assess, using objective means, pain level and also determine the safety of drug or other forms of treatment. Utilization of the automated system provided herein, decreases the possibility of abusing pain medication and the acute and chronic adverse effects of this behavior.

Before we turn to description of the various figures, several terms used throughout the disclosure will be described. Generally, a "pain level" as used herein refers to an amount of pain, as determined by subjective reporting by a patient. The pain level indicates the conscious perception of intensity and quality of pain reported by the patient in verbal and/or non-verbal language and is associated with an emotional state and behavior that may or may not be strongly (positively or negatively correlated) with the frequency, amplitude and pattern of activity of neuronal processes and systems responsive to noxious stimuli.

A "pain index" refers to a value determined from a body signal indicative of and/or correlated with a pain level. Exemplary body signals may include blood pressure, heart rate variability, respiration rate, etc. Numerous other body signals are given infra. These signals are usually outside the patient's realm of consciousness (i.e., generally, the patient lacks awareness about them and as such the signals are not verbally reportable).

Pain range refers to gradations of pain a patient may feel. A "pain perception threshold" herein refers to a value or intensity of a noxious stimulus at which a patient perceives pain of a particular magnitude or severity and quality. Such a threshold, that is either directly or indirectly measurable/quantifiable, is a separatrix between either a) a pain state and a pain-free state; or b) two or more pain gradations or levels. Put another way, this disclosure acknowledges a multiplicity of pain thresholds, rather than a single one.

"Empirical pain thresholds" may refer to an intensity and/or quality of a stimulus applied during a test at which patient perceives pain that may be subjectively or objectively (e.g., using body signals) gradable. "Distress threshold" and "suffering threshold" are usually associated with higher pain levels or pain indices at which the patient is in distress and/or suffering, as discussed infra.

A "therapy threshold" herein refers to a pain level or a value of a pain index at which a therapy for pain is delivered. A pain index threshold relates to an objective measure derived from body data (e.g., heart rate, kinetic activity, etc.) at which pain therapy may be initiated. A pain index threshold may correspond to a patient's subjective "pain threshold," or it may be different because, being subjective, pain thresholds may fluctuate while pain index thresholds may only change by manual programming or an adaptive response to factors, such as emotional state, fatigue, or the like, to maintain a desirable correlation with the subjective pain threshold. A "discomfort index" herein refers to a value determined from a body signal indicative of and/or correlated with a patient's physical discomfort level.

Turning now to FIG. 1, a stylized depiction of a medical device 100 capable of delivering therapy, in accordance with one embodiment of the present disclosure, is illustrated. In one embodiment the medical device 100 is external to the patient and capable of delivering medication using a variety of methods, such as an i.v., mucosal (e.g., nasal, rectal), serosal (e.g., peritoneum) or dermal interface. Alternatively, the medical device may be fully implanted into the patient's body to deliver a therapy (e.g., electrical stimulation, drugs) directly to a target.

A medical device system may comprise one or more sensors 140 that are connected to the medical device 100 via a communication means 130. The communication means 130 may comprise various types of communication conduits, such as medical leads, wires, wireless connection, etc. The medical device 100 may also be coupled to one or more delivery points 110, such points 110 each comprising a mechanism for delivering therapy to a location in or on the patient's body. In some embodiments, the delivery point 110 may include a needle for delivering medication, a catheter, nasal prongs, etc. The delivery point 110 may be coupled to the medical device 100 via a conduit 120 for delivering medication. The conduit may be made from flexible biocompatible material to conform to the patient's body.

In one embodiment, the medical device system is capable of sensing one or more physiological signals via the sensors 140. The sensors 140 may represent a single sensor or a plurality of sensors capable of detecting various physiological signals. For example, the sensors 140 may include one or more of autonomic signal (e.g., respiratory, cardiac, dermal activity) sensors, neurological (e.g., EMG, reaction time, ocular activity, oculo-vestibular activity) signal sensors, endocrine signal (e.g., cortisol) sensors, metabolic (pH) sensors, tissue stress marker signal (e.g., lactic acid) sensors, temperature sensors, sound/acoustic sensors, etc. More detail regarding such signals and appropriate sensors may be found in U.S. patent application Ser. No. 12/896,525, hereby incorporated herein by reference.

Based upon analyses of the detected physiological or pathological signal(s), the medical device 100 may make a determination whether delivery of medication is safe and appropriate. This determination may be based upon a look up table, real-time or near real-time calculations, or may be based upon sending the physiological signal(s) to a device external to the medical device 100 and receiving feedback from the external device. For example, the medical device 100 may determine one or more of a patient pain index, based at least in part on the first sensed body signal, such as any of those referred to above; a safety index wherein the safety index is based at least in part on a second sensed body signal, such as any of those referred to above, and which may be the same as the first sensed body signal; and whether the patient pain index is approaching, at or above certain first, second, third, or fourth, etc., pain, distress or suffering threshold(s) for the patient.

A patient pain index is used herein to refer to any objective body signal measurement correlated with pain. Exemplary objective body signal measurements include, but are not limited to, changes in heart rate, changes in heart rate variability, changes in respiratory rate, respiratory pattern, tidal volume, changes in dermal activity, changes in activity of facial muscles and muscle groups used in frowning, wincing, cringing, or other facial expressions suggestive of pain (e.g., the corrugator supercilii) or distress/suffering, which may be measured by electromyography (EMG) or imaging (e.g., video-thermography), voice analysis, the occurrence of non-formed vocalization or utterances associated with or suggestive of pain or of distress/suffering, changes in electrical, chemical, thermal brain activities or their output functions (e.g., attention, memory, etc.), or the results of responsiveness and/or awareness tests. These changes in body signal values may be determined in reference to pain-free-state signal values in the absence of any therapeutic intervention as well in reference to the cause of pain, site/location of pain and extent of body involvement, type of pain (e.g., burning, boring, electric-shock like), relation of pain to body/joint position or level of activity, time of day, anxiety level, age, gender, the psychological reaction of the patient to pain and the patient's coping skills, personality type/psychological profile, or to other factors known to alter pain threshold/perception. Pain indices may be also estimated in reference to other pain levels or different pain types, yielding relative pain indices.

The various thresholds regarding the pain index may be based on quantitative or qualitative factors, e.g., they may reflect particular changes in heart rate, heart rate variability, etc., and/or they may reflect patient perception or conscious awareness, as well as the level of distress or suffering the patient experiences. For example, in an initial workup, the amount of pain which the patient perceives (is aware of if he or she so chooses, e.g., is mild enough to be ignored if he or she so chooses) or is conscious of (is aware of regardless of his or her choice, e.g., is intense enough that he or she cannot ignore it) may be determined and correlated with particular increases in heart rate, heart rate variability, etc.

Because the intensity, duration, or type/quality of stimuli required to cause pain or the susceptibility to feeling pain is not constant, the pain and/or distress/suffering thresholds vary as a function of one or more of: a) time of day; b) level of consciousness (wakefulness v. sleep); c) level of cognitive activity (inattentive v. attentive); d) psychological status/personality; e) body site where pain occurs or to where noxious stimulus/stimuli is/are applied when estimating pain and/or distress/suffering thresholds; f) number of body sites and/or extent of body where pain occurs or to where noxious stimulus/stimuli are deliver to estimate pain and/or distress/suffering thresholds; g) type of treatment/drug and time of last treatment; h) efficacy of treatment determined using subjective (pain scales) or objective (body signals); i) environmental conditions (e.g., room temperature); j) prevailing psychological conditions (e.g., tense situation); or k) changes in body signals indicative of pain as a function of the factors listed in this paragraph.

Regarding perception or awareness of pain and the reaction (e.g., suffering) to it, these phenomena occur when pain impulses reach the cortex (SS1, limbic system, and others). Blockage of pain impulses to the cortex may prevent the perception and/or consciousness of pain. The perception of pain may be associated with an emotional response of distress, discomfort, or suffering. If the emotional response is treated, the patient may experience relief even while perceiving pain. In several embodiments, this disclosure may address the emotional correlates of pain and/or the blockage of perception of pain.

In one embodiment, the pain threshold is divided into or classified as subjective and objective. Subjective threshold is that at which the patient is first aware of an uncomfortable or painful sensation, or of an increase in said painful sensation, when noxious stimuli are being delivered at higher intensities (while taking precautions to avoid accommodation/habituation) to a body part or location. Objective pain threshold is that at which changes in indices derived from body signals (e.g., cardio-respiratory, kinetic, dermal activity) compared to a reference value, first occur or of a further increase in said indices or body signal when noxious stimuli are being delivered at higher intensities (while taking precautions to avoid accommodation/habituation or injury) to a body part or location.

The subjective (e.g., what the patient reports) and objective (e.g., the magnitude of change and/or the rate of change in an index or body signal) thresholds are estimated by presenting noxious stimuli to the patient at one or more body sites at different times and/or dates while recording the level of consciousness, psychological state of the patient, and immediate (e.g., where the patient is at the time of testing) environmental conditions among others. The difference in noxious stimuli intensity, if any, between the subjective and objective thresholds is recorded and may be used to: 1) estimate the degree of discrepancy between objective and subjective perception; or 2) use this difference for prophylaxis of pain. For example, if changes in body signals (or indices derived therefrom) occur under certain conditions at intensity levels below those associated with pain perception, therapy may be delivered as soon as changes in the body signal or index occur, preventing the perception of pain.

In another embodiment, pain perception by the patient and/or changes in indices or body signals are compared to the latency, magnitude (amplitude and duration), morphology, polarity, and topography of nerve root, spinal cord, or brain responses elicited by the noxious stimuli. Analyses of these signals, a multi-variate approach to pain management, may provide valuable information about subjective and objective components of pain. Changes in the magnitude of the differences between the subjective and objective threshold, or changes in any of the thresholds, may be used to assess pain status, issue a prognosis, or determine if there is progression or improvement. For example, if the intensity of noxious stimuli required to elicit pain perception and/or changes in body signals decreases as a function of time, pain is worsening and measures may be instituted to decrease the probability of evolving towards severe/chronic pain syndrome. The methodology to determine a threshold entails the delivery of stimuli at the lowest possible intensity (so-called sub-threshold intensities) and gradually increase said intensity, until pain is perceived or changes in body signals are recorded. Noxious stimuli may be electrical, mechanical (e.g., pressure), thermal or chemical. While only intensity has been mentioned, other properties or characteristics such as quality, frequency, duration, etc., may be varied to determine thresholds.

Other thresholds may be used (and determined) in this disclosure for the purpose of managing pain to minimize or abolish not only this sensation but its associated distress or the feeling of suffering, intolerability/un-endurability (e.g., when pain becomes unbearable, agonizing). Distress/discomfort and suffering/intolerable/agonizing are regarded as being distinct from each other in this disclosure and each state may be also classified as subjective and objective. Subjective distress threshold is the intensity or stimulus property/characteristic at which the feeling of distress is first felt or perceived. An objective distress threshold is the intensity or stimulus property/characteristic at which body signals (or indices derived from them) susceptible to influence by distress further change or reach a particular value indicative of distress.

Subjective suffering threshold is the intensity or stimulus property/characteristic at which the feeling of suffering/intolerability is first felt and an objective suffering threshold is the intensity or stimulus property/characteristic at which body signals/indices susceptible to influence by suffering further change or reach a particular value indicative of suffering. The intensity or properties of the noxious stimuli required to elicit the perception of non-distressing pain, of distressing but bearable pain, or of suffering/unbearable pain may be the same or different for a given patient and may vary as a function of time of day and psychological state, among other factors. These findings sheds light and insight into the psychological make-up, pain coping mechanisms and resilience of the patient to pain and may help shape the pain management strategy and the issuance of prognosis (e.g., will the patient develop a chronic pain syndrome?). It is common knowledge or experience that the sensation of pain (depending on its intensity, type, location, time of day, level and type of activity the person with pain is engaged in, the person's mood, environmental conditions, etc.) may be ignored and the person may continue to function normally, or the pain may be bearable but cause distress and affect the person's functional capacity to some extent, or the pain may become crippling/insufferable and the person is unable to engage in any activity, the pain becoming the sole focus of that person's attention or life. It is also known that the higher the intensity or the more noxious the stimulus, the more distress or suffering is experienced by the patient. It is therefore useful for treatment and prognostic purposes to determine if there are differences in the intensity or properties of stimuli that elicit the sensation of: a) pain only; b) pain and distress; c) pain and suffering. If a stimulus intensity that initially caused only pain now causes distress or suffering, this points to a worsening of the condition. While as stated above, the intensity/properties of the pain play a role in determining whether or not distress or suffering ensue, other factors innate to the person and to the environment may also shape the response. Distress and suffering thresholds may be determined using the methodology for determination of subjective and objective thresholds.

A subject's ability to perform certain physical tasks (e.g., perform a certain range of joint motion, lift a certain weight, walk a certain distance at a certain speed) or cognitive tasks (e.g., complex reaction time tests, attention span tests) may be also used to grade the intensity of pain and its impact of the subject's functional abilities.

A safety index is used herein to refer to a quantitative estimate of the safety of a pain treatment. For example, the safety index may depend on one or more of the pain treatment regimen (e.g., type, specific drug if the type is medications, dosages of drugs, rate of administration, etc.), the patient's age, weight, body mass index (BMI), sex, other health conditions, wake/sleep status, etc. A safety index may be calculated or determined using at least one of the body signals that are susceptible to change by drugs or therapies for pain; vital signals (e.g., heart rate, blood pressure), cognitive functions (e.g., performance on complex reaction time tests, responsiveness tests, or awareness tests; or indicators of alertness or drowsiness), vestibulo-cerebellar functions, are among those most affected by analgesics. Such signals and indicators may be considered by their absolute value (e.g., an indicator of a particular level of consciousness or of greater of drowsiness may be taken into account when administering a CNS depressant drug) or their relative value (e.g., a decrease in heart rate of n beats per minute below baseline may be taken into account when administering a narcotic). For example, an increase in mean latency in response time to reaction time tests may be used to quantify a change in safety index. In general, a safety index may be computed, for example, as the algebraic sum of changes in value in one or more values determined from body signals, compared to reference (off-drugs) values.

Returning to FIG. 1, the medical device 100 may be capable of receiving inputs from the patient for a request for medication. The input may be received via the sensors 140, or other type of input means, such as wireless communication means, tap sensors, magnetic sensors, etc. Based upon a request from the patient, the medical device 100 may perform an evaluation of one or more physiological or pathological signals of the patient's body to determine whether it would be safe and appropriate to deliver medication to the patient. In this manner, abuse of pain medications may be curtailed and the patient's safety protected. If a determination is made from the analysis of the physiological or pathological signals that there are no detectable pain correlates, the medical device 100 may not deliver medication to the patient. Further, the medical device 100 may automatically log to memory and/or report this event to a predetermined location, such as a nurse's station or monitoring center. A medical professional may retrieve this information to evaluate the patient's behavior tendencies, treatment efficacy, etc.

For the sake of clarity regarding the use of "safety" and "drug tolerance" herein, because the present disclosure is focused on pain management, such as by drugs that relieve pain (e.g. narcotics), the term "tolerance" is used herein to describe a therapy's loss of analgesic effect with repeated administration. Unpleasant or deleterious side effects that may be caused by the therapy are considered here under the rubric "safety." "Safety" also means no drop in vital signs to a level that may cause physiological dysfunction to the patient and/or lethargy, confusion, incoordination, falls or injury.

Discussions herein of tests of safety take into account the present condition of the patient and, based on that condition, pain therapy may be withheld or modified. As a hypothetical, non-limiting example, consider an elderly patient with a baseline resting blood pressure of 140/90; pulse of 80; respiratory rate of 12, cognitively intact, no motor or visual deficits, and in pain with no prior treatment for it. Beginning automatic delivery of a narcotic while monitoring the vital signs, it may happen that after 3 mg of fentanyl, the patient's blood pressure drops to 110/60; infusion may then be stopped since it is causing "hypotension" for that individual. For another example, consider the same patient awake and ambulatory at home, when fentanyl infusion begins. After 5 mg, the patient becomes drowsy (as determined by a reaction time test) and unsteady (as determined by body sway/oscillations recorded with an accelerometer when he stands up, oscillations that had not been present before administration of said drug). In this case, infusion may be stopped, a warning may be issued, and data may be logged for later use by a physician to determine whether different drugs should be used or whether the dose or rate of fentanyl delivery should be reduced to lower the likelihood of adverse effects.

The medical device 100 may store information relating to a particular patient, so that analysis of the patient's physiological information may be customized to that patient. This analysis may be dynamically adjusted so that more accurate evaluation and analysis of the patient's physiological information may be performed. This dynamic adjustment may be performed contingently (e.g., triggered by a request for medication or when there is a change in physiological signals) and/or periodically by a healthcare professional or automatically.

In one embodiment, if the medical device 100 determines that pain medication is warranted (e.g., based on one or more body indices), and that its delivery would be safe to the patient, with or without being prompted by a request by the patient, the medical device 100 may begin a medication delivery process. For example, the medical device 100 may activate a mechanical process to release stored medication from a reservoir. The medication may be delivered via the conduit 120 to the delivery point 110 to medicate the patient. The decision to deliver the medication, type of medication, dose, rate of delivery as well as the time of occurrence of the delivery, may be logged and/or reported to a predetermined target, e.g., the patient's physician. The automation and control afforded by the medical device 100 allows this system to be safely used in locations that are remote from the healthcare facilities, e.g., usage in a home-health context.

Although FIG. 1 refers to the delivery of pain medication, the medical device 100 may be configured to deliver any pain treatment, not necessarily a pain medication. For example, the medical device may be configured to select a pain treatment regimen comprising at least one of a medication, a dose of the medication, a delivery route of the medication (e.g., intravenous or intrathecal), a cocktail of medications, a dose of the cocktail, a delivery route of the cocktail (e.g., intravenous, intrathecal, or intracerebral), an electrical stimulation, at least one parameter of the electrical stimulation, a target tissue of the electrical stimulation, a cognitive therapy (e.g., biofeedback/operant conditioning, or psychotherapy, among others), at least one parameter of the cognitive therapy, a biofeedback, at least one parameter of the biofeedback, a thermal manipulation, at least one parameter of the thermal manipulation, or a target tissue of the thermal manipulation; and deliver the pain treatment.

Also, the medical device may be further configured to make other determinations and/or act upon any determinations it may make. For example, the medical device may be further configured to determine a body tolerance index relating to a first medication or other form of treatment for the patient based at least in part on a history of the patient or a patient response to an exogenous painful stimulus. The medical device may be configured to select the pain treatment regimen based at least in part on the determination of the body tolerance index. Body tolerance may be assessed by measuring changes in the subjective or objective thresholds (pain, distress, suffering) to noxious stimuli using the approach described previously under different conditions, as body tolerance to drugs or other forms of treatment may vary as a function of one or more of a) time of day; b) level of consciousness (wakefulness v. sleep); c) level of cognitive activity (inattentive v. attentive); d) psychological status; e) body site to where noxious stimulus/stimuli is/are applied for the purpose of determining a pain threshold and assessing the development and degree of tolerance to a treatment; f) number of body sites stimulated; g) type or quality of noxious stimulus; h) type of treatment/drug, dose and time of last treatment; i) changes in body signals indicative of pain (accommodation may occur in this signal); or j) psychological or genetic makeup.

The medical device system may further comprise other components. In one embodiment, the medical device system may comprise an accelerometer configured to sense movement of the patient. Information provided by the accelerometer may be useful in adaptively adjusting the pain, distress, or suffering thresholds based on the patient's kinetic activity level (e.g., body movements), thus increasing specificity of pain detection using body signals, since physical activity and pain may alter body signal values. Use of an accelerometer, EMG, mechanogram, actigraph, imaging tools, or means of measuring force or work may be used to identify the degree to which changes in body signal values are due to pain or physical activity. Also, information derived from kinetic signals may be useful in validating or illuminating other objective data about pain and efficacy of a therapy. For example, some pain is associated with hypermotoric (increased) activity, such as pacing or fidgeting, whereas other pain is associated with hypomotoric (decreased) activity (movement worsens pain) compared to reference values. The onset of hypermotoric or hypomotoric activity may indicate the onset or worsening of pain, and a decrease in hypermotoric activity and/or an increase in hypomotoric activity after treatment may be indicative of efficacy.

Figure 2:
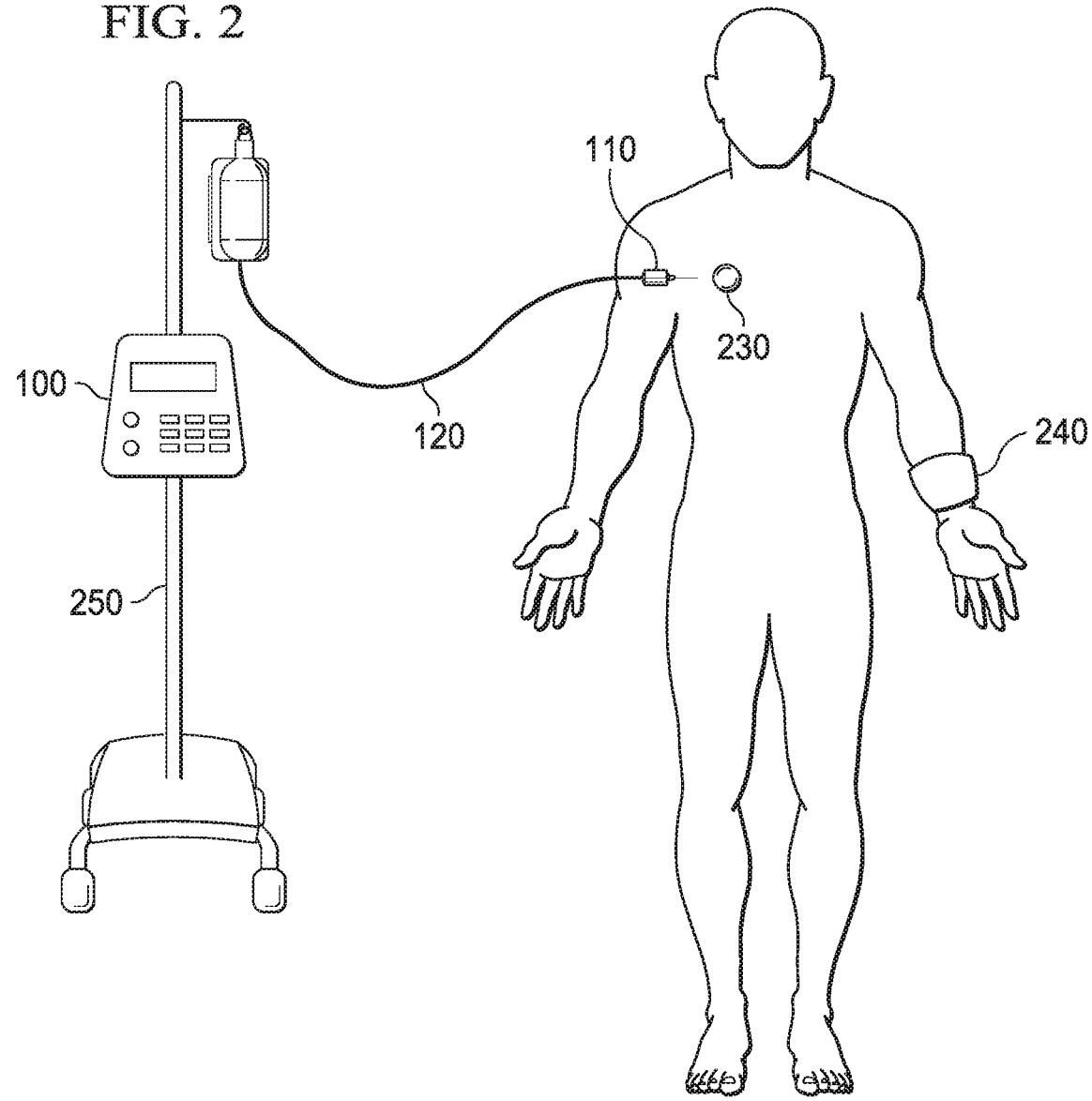
FIG. 2 illustrates a stylized depiction of an alternative configuration of the medication dispensing device, in accordance with another embodiment of the present disclosure.

Turning now to FIG. 2, an alternative implementation of the medical device 100, in accordance with one alternative embodiment of the present disclosure, is illustrated. In an alternative embodiment, the medical device 100 may be a separate standalone device that is coupled to the patient via a conduit 120, which connects the medical device 100, which in the depicted embodiment is shown mounted or otherwise connected to a rolling stand 250 to which bags or other containers of pain medication may be mounted. Conduit 120 may be coupled to the patient at the delivery point 110. In the embodiment illustrated in FIG. 2, the medical device 100 may receive physiological signals from the patient from a sensor 230, which may be capable of sensing one or more signals indicative of the patient's body data such as heart rate, blood pressure, respirations, responsiveness level/reaction time, kinetic activity, etc. The sensor 230 may be a wireless device that may be in communication directly with the medical device 100.

Alternatively, the sensor 230 may be in communication with an intermediate device 240 that is capable of receiving signals from the sensor 230 and transmitting signals to the medical device 100. The intermediate device 240 may be a signal repeater device, a signal amplifying device, a handheld device, a cell phone device, a personal digital assistance (PDA), a computer device, or a wrist device, such as a smart wristwatch. Alternatively, the intermediate device 240 may be a standalone device, such as a laptop computer, a receiver/transmitter station, etc. As described above, the medical device 100 may receive physiological signals from the sensor 230 and/or the intermediate device 240, and may perform an evaluation as to whether or not to deliver medication to the patient. For example, in a patient care facility, such as a hospital, the medical device may be connected via a catheter to the patient wherein the patient is free to move the medical device using a cart and be free to move about the medical facility. All the while, the sensor may be in communication with the medical device 100 (or alternatively the intermediate device 240) such that the medical device 100 is capable of automatically delivering pain medication based on the analyses of body signals and, in some embodiments, one or more safety indices. A warning may be issued to a caregiver if delivery is deemed unsafe or unnecessary. In an ambulatory patient (one that is not under strict bed rest orders), warnings may be issued to caregivers if vital signs, confusion or unsteadiness are detected. This action allows caregivers to take steps to prevent falls and injuries.

In an alternative embodiment, the patient may provide an input to the medical device 100 via, for example, the intermediate device 240, to request medication. The medical device 100 may then perform an evaluation of the physiological signals received from the sensor 230 to determine whether it would be appropriate to provide medication. The dosage may also be adjusted based upon the evaluation of the physiological signal before medication is delivered to the patient. Alternatively, in response to the patient's request for medication, the physiological device may be transmitted (e.g., the intermediate device 240) to a healthcare professional. The healthcare professional may then respond back to the medical device 100 (either directly or via another device, e.g., the intermediate device 240) by prompting delivery of medication at a particular dosage, or denying the delivery of the (or any) dosage.

Figure 3:
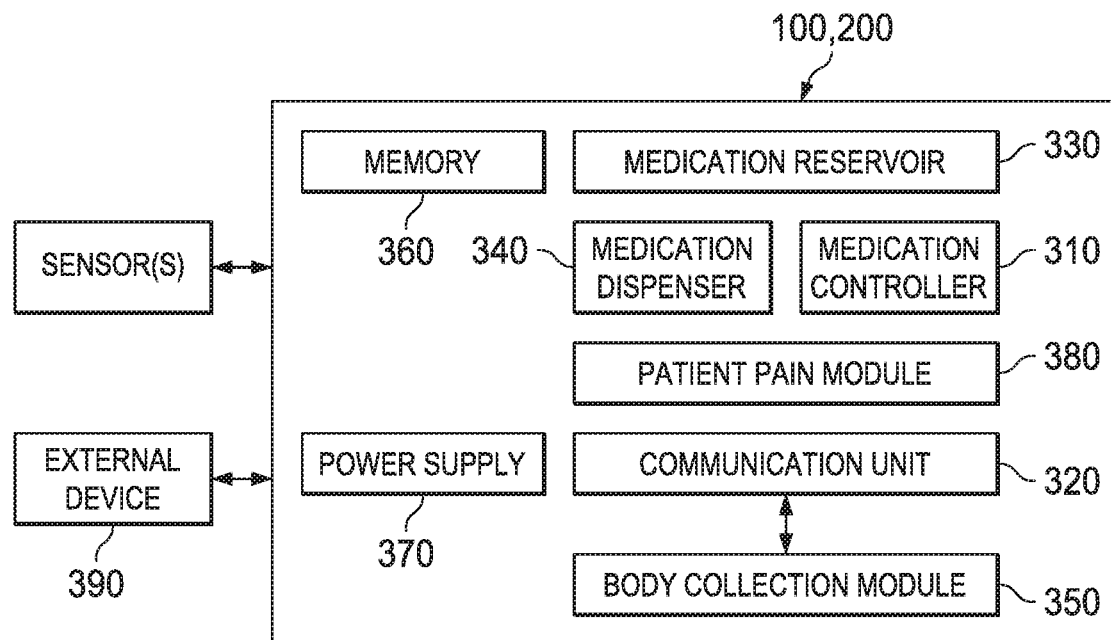
FIG. 3 illustrates a stylized block diagram depiction of the medication dispensing device of FIG. 1 and FIG. 2, in accordance with one embodiment of the present disclosure.

Turning now to FIG. 3, a block diagram depiction of the medical device 100, in accordance with one embodiment of the present disclosure, is illustrated. In one embodiment, the medical device 100 comprises a medication controller 310, a communication unit 320, a medication reservoir 330, a medication dispenser 340, a body data collection module 350, memory 360, the power supply 370, and a patient pain module 380. One or more of the blocks described in FIG. 3 may be a standalone hardware unit, a software unit, and/or a firmware unit.

The medication controller 310 may comprise one or more processors, controllers, programmable gate arrays, and/or ASIC modules. The medication controller 310 is capable of controlling various operations of the medical device 100. The medication controller 310 is capable of receiving signals indicative of pain level/intensity from the patient pain module 380. The patient pain module 380 is capable of processing one or more physiological or pathological signals from the patient's body, and/or an external signal in order to determine at least one of a pain index or a pain level. The patient pain module 380 may also be capable of determining whether the patient's subjective threshold or pain scale is supported by or in agreement with an objective threshold based on body signal data. Based upon an indication of a pain level experienced by the patient, the medication controller 310 is capable of making a determination whether it would be appropriate (i.e., indicated and safe) to provide medication to the patient at a particular time period. Autonomic and neurologic indices (e.g., kinetic, reaction time, EEG, etc.), among others, may be used to "validate" the perception of pain by a patient. Autonomic indices include but are not limited to: electrodermal/sudomotor activity, pupillary size, pupillary hippus, or R-R variability, among others.

The medication controller 310 is also capable of controlling the operation of the medication dispenser 340 and the delivery of medication from the reservoir 330. The reservoir 330 is capable of storing one or more medicinal compounds. In one embodiment, one of more medicinal compounds may be available in the reservoir 330 and mixed before delivery of medication. In one embodiment, the reservoir 330 is capable of storing medication in a variety of environmental conditions, e.g., refrigeration, pressurized conditions, etc. The reservoir 330 may have multiple compartments, each containing a type medication that is different from that in other compartments. The controller 310 may automatically dispense simultaneously more than one drug (a drug "cocktail") in the appropriate dose, depending on the patient's clinical status, pain level and type. In another embodiment, the medical device 100 may be also endowed with electrical, thermal, or cognitive/biofeedback treatment capabilities that may be used alone or in any possible combination.

The medication controller 310 may incorporate look up tables or other information in the memory 360 with regard to a particular patient's profile and the schedule of medication delivery and dose for a particular patient based upon certain variables. These variables include pain, distress, or suffering thresholds, therapy tolerance thresholds, and safety considerations (occurrence of adverse effects, their type and severity, etc.). The medication controller 310 may also perform calculations about dose and delivery schedules, based on factors such as age, gender, body mass index, fitness level, neurologic index values (e.g., kinetic, reaction time, presence and amplitude of body sway when in the upright position, presence and amplitude of nystagmus, etc.), autonomic index values (e.g., blood pressure, heart rate, respiratory rate, oxygen saturation, etc.), time from last dose and type dose of drug administered.

The medical device 100 may also comprise a communication unit 320 capable of facilitating communications between the medical device 100 and various devices. In particular, the communication unit 320 is capable of providing transmission and reception of electronic signals to and from sensors 130 external to (or implanted within) the body and/or from other external computing devices, such as a handheld computer, a laptop computer, a workstation, a desktop computer, or PDA in wired or wireless communication with the medical device 100. The communication unit 320 may include hardware, software, firmware, or any combination thereof. The communication unit 320 may comprise various components that are capable of providing for communication to and from the medical device 100. For example, interaction between medical device 100 and or more sensors 130, 230, or an external device 390 may be facilitated by the communication unit 320. The communication unit 320 is also capable of providing for wireless and wired communications between various devices and the medical device 100. These communications sessions may involve network communications or wireless communications, such as WI-FI, Bluetooth, RF, or other type of wireless communication.

In one embodiment, a medication dispenser 340 is capable of delivering medication, at a pre-specified dose and rate, from the medical device 100 to the patient. In one embodiment the medication dispenser 340 may comprise one or more pumping components that are capable of delivering medication from the reservoir 330 to a patient's body. The medication dispenser 340 may comprise hydraulic components, micro-machine components, solid state devices, electromechanical components and/or the like. The operation of the medication dispenser 340 may be controlled by the medication controller 310.

The patient pain module 380 may also comprise a body data collection module 350. The body data collection module 350 is capable of collecting various types of body of physiological or pathological data. A more detailed description of the body data collection module 350 is provided in FIG. 5 and accompanying description below.

The patient pain module 380 may comprise one or more processors, controllers, etc., capable of determining whether a particular patient's pain level is above, at, or below a predetermined pain threshold for drug delivery. Information regarding a particular patient may be stored in the memory 360, which may be utilized by the patient's pain module 380 to perform such analysis. Based upon various body data provided by the sensors 130, the patient pain module 380 may make one or more calculations to determine whether one or more body signals indicate that the patient is experiencing pain above a predetermined threshold. Further, if the patient pain module 380 were to determine that a pain index or pain level is above a threshold level, this information may be provided to the medication controller 310, which may activate the medication dispenser 340. Power for operation of the medical device 100 may be provided by a power supply 370, which may comprise one or more batteries and/or external power source. In some embodiments, power supply 370 may be rechargeable by using an external power source, a wireless inductive power source, capacitive power source, etc.

Various information, such as operation algorithms, instructions, etc., may be provided to the medical device 100 via an external device 390. The external device 390 may comprise a computer system, a controller, medication delivery devices, etc. The external device 390 may be a device that is capable of programming various modules and units of the medical device 100. The external device 390 may be controlled by a healthcare provider, such as a physician, at a base station in, for example, a nurse's station or a doctor's office. The external device 390 may be a computer, such a handheld computer, a PDA, a smartphone, etc., but may alternatively comprise any other device that is capable of electronic communications and programming. The external device 390 may download various parameters and/or program software into the medical device 100 for programming the operation of the medical device 100. The external device 390 may also receive and upload various status conditions and other data from the medical device 100. Communications between the external device 390 and the communication unit 320 may occur via a wireless or other type of communication.

Figure 4:
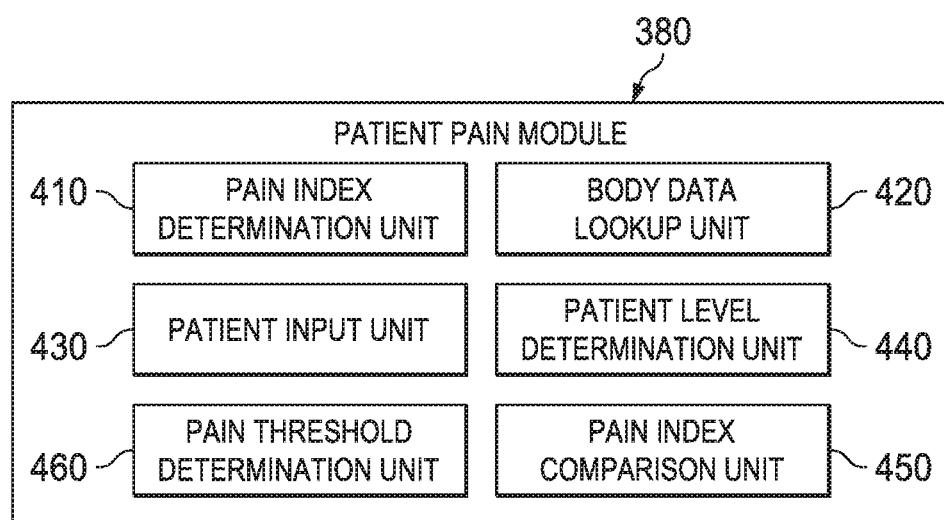
FIG. 4 illustrates a stylized block diagram depiction of the patient pain module of FIG. 3, in accordance with one embodiment of the present disclosure.

Turning now to FIG. 4, a block diagram depiction of a patient pain module 380, in accordance with one embodiment of the present disclosure is illustrated. The patient pain module 380 is capable of processing a variety of types of body data. The patient pain module 380 comprises a pain index determination unit 410, a body data lookup unit 420, a patient/caregiver input unit 430, a pain level determination unit 440, and a pain index comparison unit 450. A pain index may be computed as the difference or the ratio between observed and reference values of a body signal. For example, if the heart rate in patient in a recumbent position during a pain-free period is 65 bpm (reference value) and sometime later with the patient in the same position it is 85 bpm, the value of the pain index is +20 (the difference) or 1.3 (the ratio). If the difference between observed and reference value is used to set the therapy threshold, under those specific conditions (e.g., recumbent position) at 80 bpm, a therapy will be automatically delivered, if safe, when the recumbent heart rate reaches 80 bpm (if no duration constraint is applied). Duration constraints may be imposed for any threshold-based automated action or decision to avoid false detection of pain thresholds associated with short-lived non-specific perturbations in indices or body signals of interest. Therapy delivery may be governed not only by a pain index value (e.g., the heart rate reaching 80 bpm in this example) but also by time; the caregiver may decide that therapy will be delivered only if the heart rate remains at a minimum at 80 bpm for 15 sec. This time constraint may be also applied to changes in pain indices, where a change in value leads to an action only it remains at a certain value for a certain duration (>0 sec.)

The pain index determination unit 410 may determine one or more pain indices based upon the body data received by the medical device 100. For example, various types of body data, such as autonomic data, neurological data, endocrine data, metabolic data, tissue stress marker data, etc., may be processed and analyzed by the pain index determination unit 410. The autonomic data may include heart beat data, blood pressure data, respiration data, blood gas data, etc. The neurological data may include kinetic patient data, such as data from an accelerometer or an inclinometer, etc. Other types of neurological data may include data about the level of responsiveness or awareness of the patient. Additional types of neurological data include facial mimetic data. Further endocrine data, metabolic data, and various tissue stress marker data may be analyzed by the pain index determination unit 410. The body data received by the body data collection module 350 (FIG. 3) may be analyzed and organized by the pain index determination unit 410.

Figure 13A:
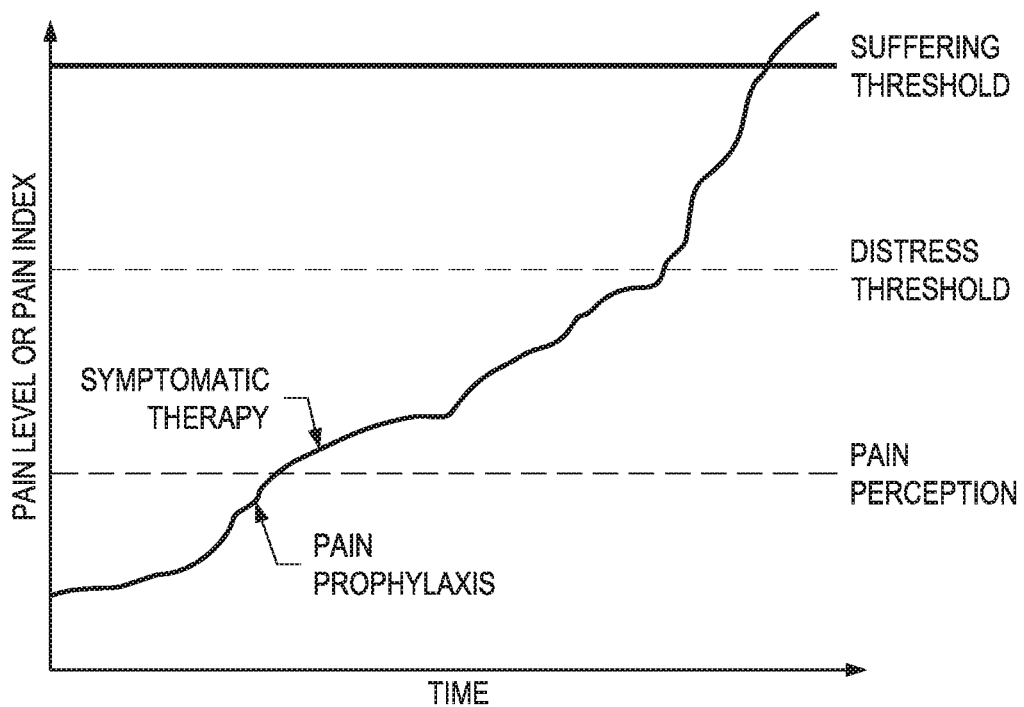
FIG. 13A illustrates the non-stationarity of pain thresholds, in accordance with one embodiment of the present disclosure.
Figure 13B:
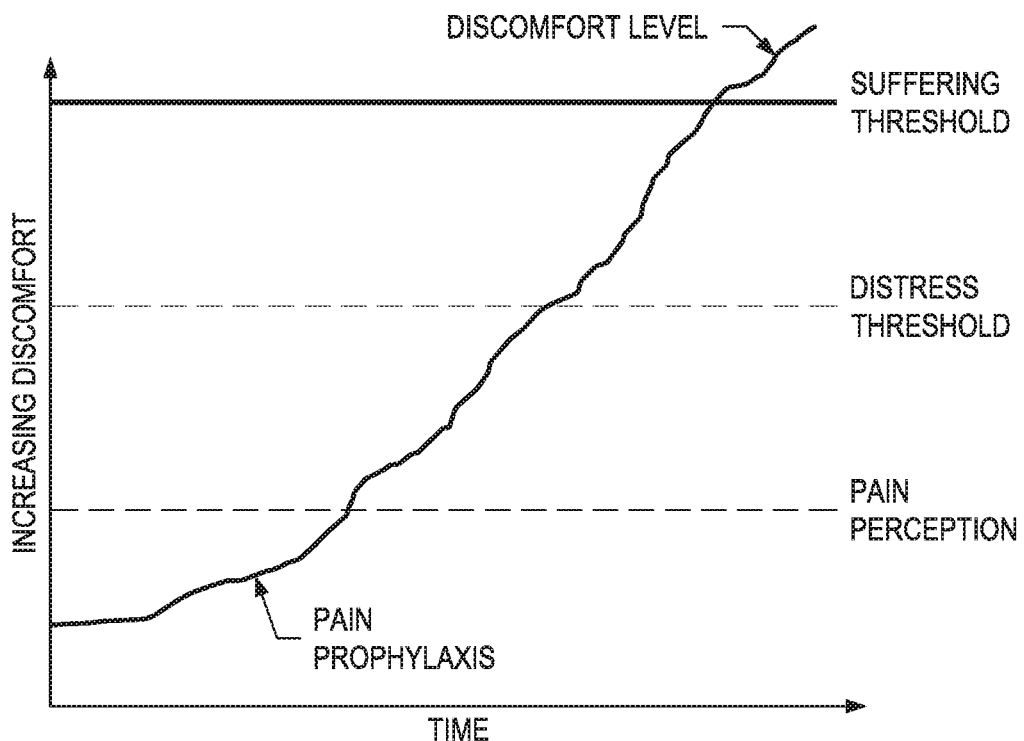
FIG. 13B illustrates the non-stationarity of pain thresholds, in accordance with one embodiment of the present disclosure.

In one embodiment, a pain index may be calibrated, validated, or corroborated by delivering noxious stimuli to the patient. The determination of a pain threshold, which may span a wide range (e.g., FIGS. 13A-13B), may be prompted by a change in at least one body signal or it may be performed according to a pre-specified schedule, or at the patient's or caregiver's discretion. To determine a pain perception, distress or suffering threshold, the patient may be fitted with a device or apparatus that generates uni- or multi-modal noxious stimuli and the mode(s) will be selected based on the patient's description of pain quality (e.g., burning, boring, electric-shock like). This device may generate one or more of mechanical (e.g., pressure, friction), thermal (e.g., cold, heat), visual (e.g., light colors and/or intensities), acoustic (e.g., loud high pitch sounds), chemical (e.g., capsaicin), or electrical stimuli that are applied in a desired combination of modes and/or intensities to mimic the patient's perceived pain, to more accurately characterize the patient's pain threshold(s). The minimum noxious stimulus intensity required to cause a painful sensation establishes the pain, distress or suffering thresholds at the time the test is administered. Because the duration of application of the pain stimulus can itself affect the pain threshold established by the test, the stimulus intensity may be increased (rapidly or slowly) during the threshold test(s).

Additionally, the conditions of the patient's immediate environment may be modified during the pain threshold test to more closely resemble those to which the patient is more often subjected, (or will be exposed to upon discharge from a medical facility) to better tailor a pain treatment plan specific to the patient. For example, if the patient's environment is acoustically noisy, determination of pain threshold may be made under acoustically noisy conditions. To better treat a patient, the determination of pain threshold may be made while presenting stimuli with negative emotional content (e.g., fear, anxiety, etc.) in the form of visual, auditory, olfactory, or tactile stimuli in any desired combination, since these negative stimuli tend to alter pain, distress or suffering thresholds. When establishment of distress and/or suffering thresholds are impractical or impossible, changes in these thresholds may be inferred from changes in the pain perception threshold as well as through administration of psychological, emotional and other tests.

Consider the following hypothetical example. A patient reports an increase in pain: a) from being free of pain to a "first"/lowest pain level (e.g., perception of tolerable pain); b) from first to "second"/intermediate pain level (from tolerable to intolerable pain/distress); c) from second to "third"/highest level (e.g., from distress to suffering) (Notice that progression need not be continuous (e.g., $1^{st}$ to $2^{nd}$ and $2^{nd}$ to $3^{rd}$), but may be discontinuous ($1^{st}$ to $3^{rd}$). In response to said increase in pain, noxious stimuli are delivered to patient whom is asked to grade their intensity. The response is compared to reference values (obtained at earlier times under certain conditions (e.g., time of day, time from last dose, mood, etc.) and used to determine if the pain intensity has indeed increased or if the sensory or the pain thresholds have decreased. For example, a thermal stimulus (heat via laser) may be applied to the dorsum of the patient's left hand and its threshold for perception is determined ("tell us when you feel heat"), while body signals may be simultaneously monitored and used in a quantitative comparison. If the patient perceives the heat at a lower intensity than before, the threshold is now lower. It may not be ethical (or useful) to determine distress or suffering thresholds, but this is not necessary, since changes in sensory or in the lowest pain threshold are likely reflect changes in the distress and suffering thresholds. Reflex responses such as rapid withdrawal of an extremity form the pain source, or actions to shield it from said source, may be used instead of verbal responses.

Sensory threshold in this disclosure is the lowest stimulus intensity/energy eliciting a conscious sensation; furthermore, sensory threshold is herein divided into painless and painful, a division that takes into account the fact that under normal conditions, that may or may not apply to patients with pain, the stimulus intensity or energy, and thus the threshold, required to elicit a non-painful sensation is lower than that required to elicit a painful one.

Returning to the hypothetical example immediately above, patients may be also presented with images, sounds, smells, or narratives with negative emotional (or positive) emotional contents and their subjective and objective responses (body signals) recorded and logged for comparisons, for determination of the stability (or lack thereof) of pain or other thresholds and indirectly of pain levels. This allows estimation of the "emotional" threshold and may be used to anticipate and prevent the perception of pain or its escalation into distress or suffering. The same comparison may be made when pain is improving (e.g. $3^{rd}$ to $2^{nd}$ level) and this information may be used to modify the therapy in advance of the expected change.

"Emotional state" herein refers to either a subjective state reported by the patient, that the patient can generally label as being either positive or negative, to which greater "granularity" may be added using numerical, pictorial or other scales. When exogenous factors (e.g., time of day, ambient temperature, noise level, etc.) are known, changes in body signals and based on them, changes in pain indices may be better interpreted, for more accurate correlation with pain levels (e.g., tolerable, distress, or suffering) or pain thresholds. By taking such exogenous factors into consideration in some embodiments, body signals and/or pain indices may be more effectively employed either to prevent transitions from one pain level to another (including the transition from a pain free into any of the other pain states) or to institute rapid treatment if prevention of the transition is not feasible. Exemplary changes may be in the body signal's magnitude, rate of change, direction (e.g., increase/decrease) and/or duration compared to a reference value.

As should be apparent, the patient's pain threshold and related concepts are generally nonstationary.

The results of patient pain threshold testing may be used to select those indices that best reflect the presence and intensity/quality of pain, to calibrate or adjust pain indices, to set pain index thresholds, and/or to make decisions about the type, dose, and schedule of delivery of a pain treatment regimen.

Figure 14:
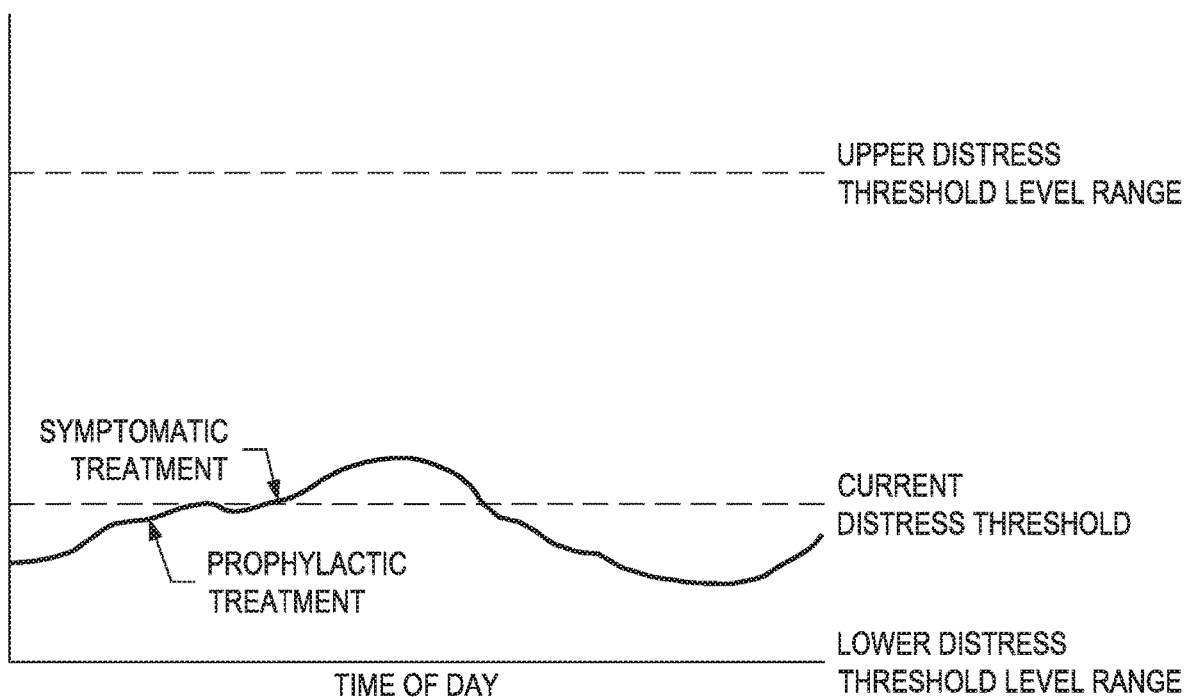
FIG. 14 further illustrates the non-stationarity of distress thresholds, in accordance with one embodiment of the present disclosure.

Determination of pain threshold(s) may be performed to:
1. deliver analgesic therapy prophylactically to the patient before the pain threshold decreases to a level likely to be associated with the perception of pain, or before the pain causes a certain level of distress, in response to a change in its value indicative of its closer proximity to an undesirable value (FIG. 14, prophylactic treatment) or symptomatic (i.e., it relieves the patient's distress) (FIG. 14, symptomatic treatment.); 2. minimize both intensity and duration of the experience of pain if prophylaxis is not possible.

It should be noted that herein, pain intensity and pain threshold are treated as variables. Pain intensity is used herein to refer to the frequency and amplitude of neural impulses traveling through the spino-thalamic and other tracts mediating the sensation of pain. Pain threshold is used herein to refer to the inherent level at which certain impulses are perceived as pain by the patient, and may vary according to many factors such as time of day, medications taken by the patient, age, sex, genetic factors, psychological factors, health and fitness levels of the patient, etc. Certain thalamic strokes manifest with spontaneous and continuous pain on the side of the body contralateral to the stroke; this is an example of reduction in the pain threshold to the point that non-noxious stimuli (e.g., touching the patients skin) become painful. Allodynia is another example of reduction in pain threshold. Pain intensity may vary but one or more pain thresholds (pain, distress, suffering, etc.) may remain constant, or pain intensity may remain constant but one or more of the thresholds may vary (increase or decrease).

This comprehensive approach disclosed herein, which takes into account an ignored patho-psycho-physiologic feature of pain, may be used to provide more intelligent and better management of pain, as it allows anticipation of changes in pain perception and the patient's response, and for the prevention and/or prophylaxis of such changes, and the patient's responses thereto. Changes in the threshold for distress or suffering may also occur throughout the day as a function not only of factors associated with circadian rhythms but also of the psychological and physical environments/conditions. For example, intense heat and being in a crowded noisy and tense environment may precipitate a sense of distress or even suffering in someone who is in pain or may make pain the center of attention in someone who was previously "indifferent" to it.

Further, the patient pain module 380 may acquire data from the memory for categorizing and analyzing the body data. For example, body data lookup unit 420 may interface with the memory 360 (FIG. 3) to perform various lookup functions, such as table lookup, etc. The pain index determination unit 410, in conjunction with the body data lookup unit 420, may analyze, process, or otherwise prepare a pain index value for use by further units of the patient pain module 380.

Moreover, an input by the patient or a caregiver relating to a request for a therapy may be detected by the patient input unit 430. The patient input unit 430 may determine the frequency of any requests from the patient for therapy, a dose delivered in the most recently provided treatment, time elapsed since the last treatment, etc., in performing the pain analysis.

The pain level determination unit 440 is capable of determining a pain level experienced by the patient based at least in part on input from the patient. In contrast to pain indices derived from body data of the patient, the pain level has at least a partial subjective component. For example, the pain level may be determined from pain scales, questionnaires, or the like. Alternatively or in addition, the pain level may encompass indicators of patient distress, i.e. psychological, social, and/or spiritual concerns that can extend from feelings of vulnerability, sadness, and fear, to depression, generalized anxiety, panic, isolation, despair, or a spiritual crisis. Emotional correlates of pain such as suffering, distress, etc., may be determined by recording body signals indicative of levels of activity of the patient's: a) kinetic activity (e.g., fidgetiness, restlessness); b) facial mimetic expression (e.g., frowning, crying, etc., any of which may be recorded using electromyography (EMG) of the effecting muscles or an imaging modality (visual, infrared, etc.) of the facial expression); and/or c) autonomic system (e.g. dermis, cardio-vascular, respiratory activity), so that a pain level may be estimated. The following scales may be used to aid in the assessment of levels of pain and distress: McGill Pain Questionnaire; Facial expressions;

Happy/sad face graphic pain scale; Analog scale for patient self-assessment; Numeric Rating Scale; Wong-Baker Faces; COMFORT Scale; CRIES Pain Scale; FLACC Scale; Checklist of Nonverbal Indicators; Pictorial representation of illness and self-measure; Visual Analog Scale; Graded Chronic Pain Scale; the Hospital Anxiety and Depression Scale and the Insomnia Severity Index; Likert scale; Functional Assessment of Chronic Illness Therapy-Spiritual Well-Being; Edmonton Symptom Assessment Scale; Structured Interview Assessment of Symptoms and Concerns in Palliative Care Distress; Hamilton Depression Rating Scale; Will to Live and Desire for Death Visual Analogue; Schedule of Attitudes toward Hastened Death; Desire for Death Rating Scale. Other means to assess distress, depression and/or suffering and their impact on the patient are (listed in no particular order):

Mini-Suffering State Examination (MSSE). Total mood disturbance scores of the Profile of Mood States, FACIT-Sp, Schedule of Attitudes toward Hastened Death, Desire for Death Rating Scale, The FACIT Quality of Life measure, the Missoula-VITAS Quality of Life Index, the McGill Quality of Life tool, the QUALE, the EORTC questionnaires/(QLQ-C15-PAL), the Functional Assessment of Cancer Therapy modules, the Quality of Life Scale, the Diagnostic Interview Schedule, the Composite International Diagnostic Interview, the Schedule for Affective Disorders and Schizophrenia, the Endicott Substitution Criteria, the Diagnostic Interview Schedule, the Composite International Diagnostic Interview, the Structured Clinical Interview for DSM-IV, the Beck Depression Inventory-13 items, the General Health Questionnaire, the Hospital anxiety and depression scale, the Centre for Epidemiologic studies depression scale, Hospital anxiety and depression scale, Beck Depression Inventory-II, the Palliative care outcome scale, the State-of-Suffering-V, or the so-called distress thermometer. A distress level threshold may be variable, being subject to influences similar to those that affect the pain perception threshold as discussed herein.

Based upon various characteristics of the body data, the patient pain index value may then be compared to a pain level or to a pain threshold by the pain index comparison unit 450, so that a degree of concordance between them may be determined (e.g., whether the pain index is commensurate with the pain level). For the comparison, the pain index value determined from body data may be compared to index values associated with one or more of the patient's pain level threshold, distress threshold, or suffering threshold to determine whether a therapy should be provided to the patient. Because the various pain levels and thresholds are non-stationary, the pain index value may be weighted before comparing it to the level or to the threshold(s) (e.g., the pain index can be given more weight the higher the concordance between it and the prevailing pain level experienced or reported by the patient), and/or the changes in threshold(s) detected and the treatment plan adjusted in light of said changes.

The therapy threshold for at which a therapy may be delivered to the patient may be provided to the pain index comparison unit 450 by the memory 360. Upon a comparison of the pain index and the predetermined threshold, the pain index comparison unit 450 may provide data as to whether a predetermined pain threshold has been crossed. Based upon the patient pain index reaching or exceeding the pain index threshold, the medical device 100 may deliver automated, predetermined therapy to the patient. Further, the medical device 100 may also store and report this action, and receive and act upon any instructions based upon the reporting. In one embodiment, subjective pain scales in an electronic device capable of communicating with pain input unit 430 may be used (subject to validation using body signal analyses) to aid in the management of pain.

A number of factors may influence pain levels experienced by the patient. These may include: a) frequency, amplitude and patterns (e.g., bursting v. tonic) along the lateral hypothalamic and other brain tracts carrying noxious signals to the thalamus; b) changes in the mechanisms that inhibit pain signals or neural plasticity-related changes that result in "amplification" of pain signals at any level of the neuraxis; and c) the emotional and cognitive modulation of pain signals at the cortical-subcortical levels. Increases in frequency, amplitude or changes in firing pattern of neurons mediating pain disinhibition or "amplification" are likely to augment the sensation of pain. Emotions, mood or behavior shape the response to pain and the patient's reaction to it. In one embodiment of this invention, factors a), b) or c) are taken into account to manage (prophylaxis and/or treatment) of pain. This may be accomplished through invasive or non-invasive monitoring in patients of electrical, chemical, thermal, photonic, mechanical (e.g., pressure, movement), cognitive/behavioral/emotional activity of nerves, roots, tracts, zones, pathways, nuclei or cortical regions, using appropriate tools (e.g., electrodes, sensors, fMIll, PET scan, scales/questionnaires, etc.). The dependence of pain level (e.g., tolerable, intolerable) on the factors listed above may be investigated by determining pain thresholds to noxious stimuli in a systematic and controlled manner.

The difference in magnitude, rate of change or "direction" of change (increases or decreases) of the value in a pain index derived from a biological signal during an episode of pain in comparison to the same index when the patient is not experiencing pain at the same or different times of day and under similar or different conditions (e.g., wakefulness; attentive state, etc.), may be used to empirically determine/quantify pain levels.

One or more composite pain indices may be determined from different types of body signals. For example, body indices from two or more different classes of signals (e.g., cardiac signals such as heart rate, heart rate variability, EKG morphology characteristics, electro-dermal or sudo-motor activity, etc.) and kinetic signals such as those indicative of a patient's movement, posture, muscle activity, etc.) may be used to derive a composite index. The composite index value during an episode of pain may then be compared to the corresponding composite index value when the patient is not experiencing pain to provide information useful in establishing or modifying a treatment regimen. Exemplary composite indices may comprise, e.g., the sum, mean, product, difference, ratio, etc., of two or more individual indices.

Pain indices (whether individual or composite) may be adjusted or corrected for numerous factors that may affect patient pain intensities and/or thresholds. Among the factors that may be used to provide such adjustments/corrections are time of day, level of consciousness, level of fitness, medication levels, age, sex, genetic factors, etc.

The patient pain module 380 may also comprise a pain threshold determination unit 460. The pain threshold determination unit 460 may be configured to determine a pain threshold for the patient for a certain modality (e.g., burning). The pain threshold determination unit 460 may determine pain thresholds from one or more body signals, whose value(s) are suggestive of sufficient pain to merit treatment with pain medications or other pain treatments. The patient pain module 380 may also be used to determine a sensory threshold (i.e., the minimal stimulus intensity required to elicit a non-painful sensation) to: 1. determine if there is a change in the sensory threshold; and 2. determine if there is a change in the intensities (computed as the differences or ratios) of the stimulus energies required to elicit a non-painful and a painful sensation. This information may be used to assess the status of the pain disorder.

In a particular embodiment, the pain threshold determination unit 460 may be configured to provide at least one stimulus to a patient, receive a response of the patient to the at least one stimulus, and determine, based on the response to the at least one stimulus, at least one pain threshold. In a particular embodiment, the pain threshold determination unit 460 may instead by configured to determine, based on the response to the at least one stimulus, whether at least one pain threshold has changed.

The pain threshold determination unit 460 may, in some embodiments, determine a distress threshold and/or a suffering threshold, by extrapolating from the pain thresholds, patient workup, and/or other data sources the values of body signals suggestive of distress (heightened pain) and/or suffering (excruciating pain).

Pain thresholds may also be affected by emotional/behavior factors, and such factors may also be used to adjust pain threshold (or pain index) values. These factors may also be determined by the presentation of stimuli with positive and/or negative emotional meaning to the patient during threshold testing (e.g., during or proximate to the presentation of noxious stimuli as part of pain threshold testing).

Returning to FIG. 3, the communication unit 320 may be configured to communicate an alert if the determined pain index is below the predetermined threshold pain index and the patient requests medication. Thus, if the pain level actually experienced by the patient at any time is incommensurate with the pain index to which the pain level usually correlates, an alert can be given to a caregiver to: a) determine if the treatment device (e.g., sensors, modules, etc.) is operating correctly; b) if the treatment device is operating correctly, re-test pain thresholds to find if they have undergone changes; c) if the threshold remains unchanged, investigate for the development of tolerance to medications; d) if the patient has not developed tolerance to medications, warn the caregiver of possible drug-seeking behavior by the patient.

Figure 5:
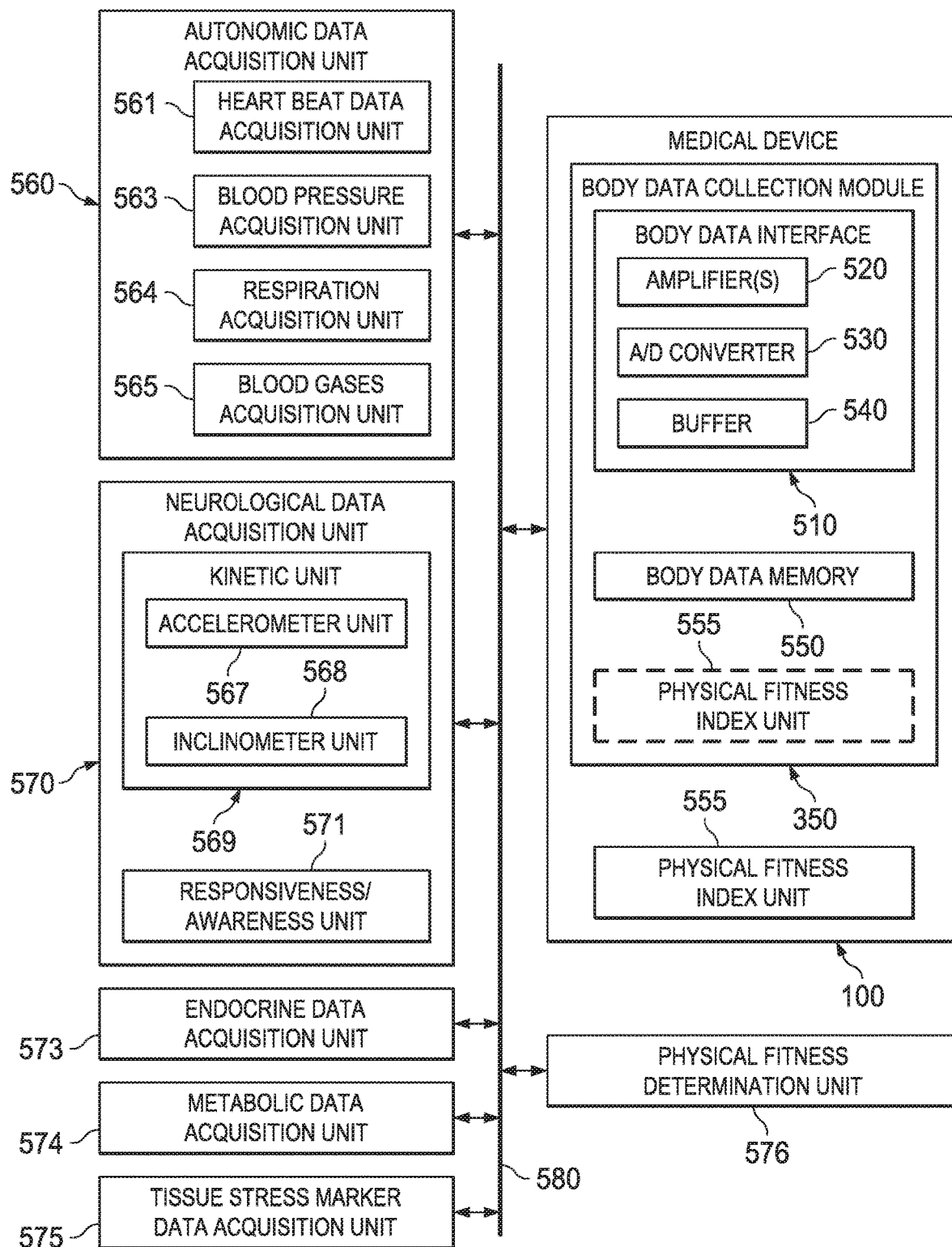
FIG. 5 illustrates a more stylized detailed block diagram description of the body data collection module of FIG. 3, in accordance with an embodiment of the present disclosure.

Turning now to FIG. 5, a block diagram depiction of the body data collection module 350 is provided, in accordance with one illustrative embodiment of the disclosure. FIG. 5 depicts an exemplary implementation of the body data collection module 350 described above with respect to FIG. 3. The body data collection module 350 may include hardware (e.g., amplifiers), tools for chemical assays, optical measuring tools, and/or a body data memory 550 for storing and/or buffering data in the body data collection module 350. The body data memory 550 may, in some embodiments, be adapted to store body data for logging or reporting purposes and/or for future body data processing and/or statistical analyses.

The body data collection module 350 may also include one or more body data interfaces 510. The body data interface 510 may provide an interface for input/output (I/O) communications between the body data collection module 350 and body data units/modules (e.g., [560-570], [573-576]) via connection 580. The body data units/modules (e.g., [560-570], [573-576]) may comprise various sensors for acquiring body signals, and may communicate with the medical device 100 via the communication unit 320 via connection 580. The connection 580 may be a wired or wireless connection, or a combination of the two. The connection 580 may be a bus-like implementation or may include an individual connection (not shown) for each, or some number, of the body data units (e.g., [560-570], [573-576]). The connection 580 may also include connection elements as would be known to one of skill in the art having the benefit of this disclosure. In various embodiments, the body data units may include, but are not limited to, an autonomic data acquisition unit 560, a neurologic data acquisition unit 570, an endocrine data acquisition unit 573, a metabolic data acquisition unit 574, a tissue stress marker data acquisition unit 575, a quality of life (QOL) unit (not shown in FIG. 5), and/or a physical fitness/integrity acquisition and determination unit 576.

In one embodiment, the autonomic data acquisition unit 560 may include a heart beat data acquisition unit 561 adapted to acquire a phonocardiogram (PKG), EKG, echocardiography, apexcardiography and/or the like, a blood pressure acquisition unit 563, a respiration acquisition unit 564, a blood gases acquisition unit 565, and/or the like. Alternatively or in addition, the autonomic data acquisition unit may comprise an infrared imager to detect changes in the temperature parts (e.g., face) that may be indicative of pain.

In one embodiment, the neurologic data acquisition unit 570 may contain a kinetic unit 566 that may comprise an accelerometer unit 567, an inclinometer unit 568, and/or the like; the neurologic data acquisition unit 570 may also contain a responsiveness/awareness unit 571 that may be used to determine a patient's responsiveness to testing/ stimuli (e.g., reaction time) and/or a patient's awareness of their surroundings. Responsiveness may be determined by asking the patient to perform simple verbal (e.g., What is your name?) or motor tasks (e.g., raise your right hand), answer questions about orientation (e.g., What is today's the date; Where are you?), or more complex cognitive (e.g., complex reaction time, memory tests), and motor tasks (e.g., close your eyes, make a first with your left hand and touch your left ear with your right hand). When necessary, responsiveness may be assessed using noxious stimuli. Responsiveness may be quantified using latency to and accuracy/ correctness of responses, among others. Since certain pain medications depress the central nervous system and since decreased responsiveness precedes potentially serious or fatal adverse medication effects such as respiratory depression, bradycardia or hypotension, assessment of responsiveness is key to preventing the occurrence of these serious adverse effects.

Alternatively or in addition, the neurologic data acquisition unit 570 may also comprise a video or infrared imager with facial recognition software or facial EMG to detect changes in facial expression indicative of pain, and/or sound/acoustic sensors to detect sounds indicative of pain (such as moans/groans). These lists are not exclusive, and the body data collection module 350 may collect additional data not listed herein, that would become apparent to one of skill in the art having the benefit of this disclosure. The body data units [560-570], [573-576] may be adapted to collect, acquire, receive/transmit heart beat data, EKG, PKG, echocardiogram, apexcardiogram, blood pressure, respirations, blood gases, body acceleration data, body inclination data, EEG/ECoG, and/or the like. The quality of life (QOL) unit (not shown in FIG. 5) may be also used to assess the psychological status of the patient. Additional details on body signal analysis are provided by other patent applications assigned to Flint Hills Scientific, LLC or Cyberonics, Inc., such as, U.S. Ser. No. 12/896,525, filed Oct. 1, 2010; U.S. Ser. No. 13/288,886, filed Nov. 3, 2011; U.S. Ser. No.

13/449,166, filed Apr. 17, 2012; and U.S. Ser. No. 13/678, 339, filed Nov. 15, 2012. Each of the patent applications identified in this paragraph is hereby incorporated herein by reference.

The body data interface(s) 510 may include various amplifier(s) 520, one or more A/D converters 530, and/or one or more buffers 540 or other memory (not shown). In one embodiment, the amplifier(s) 520 may be adapted to boost and condition incoming and/or outgoing signal strengths for signals such as those to/from any of the body data units/modules (e.g., [560-570], [573-576])) or signals to/from other units/modules of the medical device 100. The A/D converter(s) 530 may be adapted to convert analog input signals from the body data unit(s)/module(s) into a digital signal format for processing by controller 210 (and/or processor 215). A converted signal may also be stored in a buffer(s) 540, a body data memory 550, or some other memory internal to the medical device 100 or external to the medical device 100. The buffer(s) 540 may be adapted to buffer and/or store signals received by the body data collection module 350 as well as signals to be transmitted by the body data collection module 350. In various embodiments, the buffer(s) 540 may also be adapted to buffer and/or store signals in the body data collection module 350 as these signals are transmitted between components of the body data collection module 350.

As an illustrative example, in one embodiment, data related to a patient's respiration may be acquired by respiration unit 564 and sent to the medical device 100. The body data collection module 350 in the medical device 100 may receive the respiration data using body data interface(s) 510 to determine its rate, amplitude, and/or pattern. As the data is received by the body data interface(s) 510, the incoming data may be amplified/conditioned by amplifier(s) 520 and then converted by A/D converter(s) into a digital form. The digital signal may be buffered by a buffer(s) 540 before the data signal is transmitted to other components of the body data collection module 350 (e.g., body data memory 550) or other components of the medical device 100. In some alternative embodiments, the body data units/modules (e.g., [560-570], [573-576])) may be housed within the medical device 100. Body data in analog form may be also used in one or more embodiments.

Figure 6:
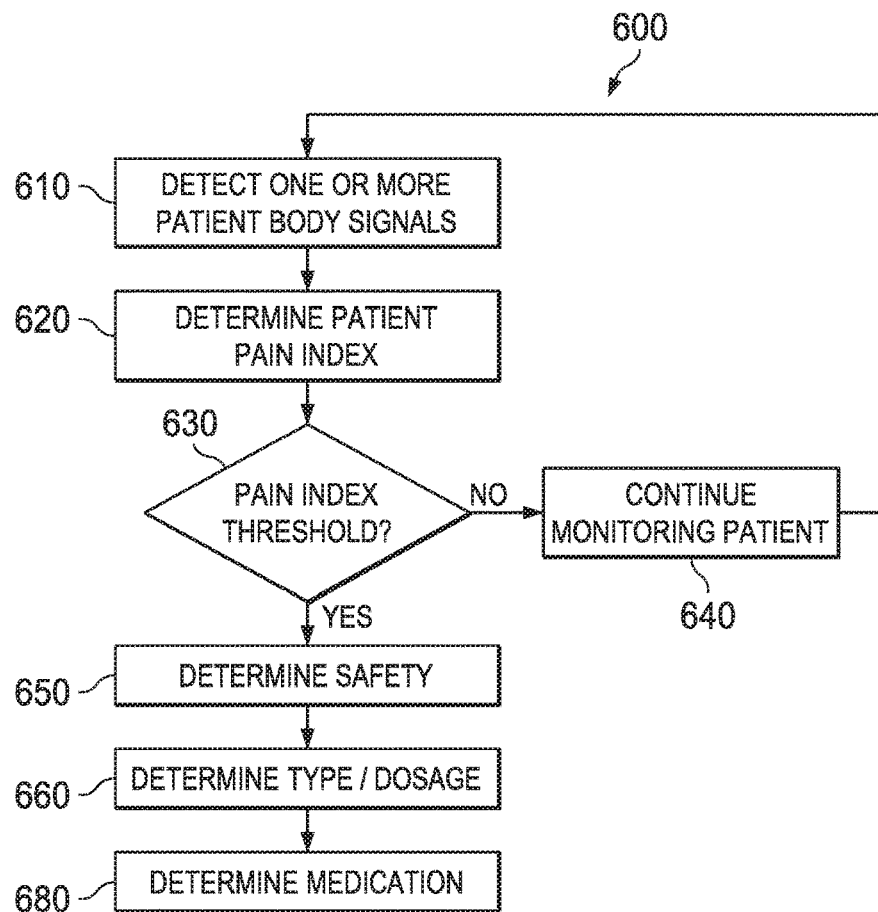
FIG. 6 illustrates a flowchart depiction of the steps for performing an automated delivery of medication, in accordance with one embodiment of the present disclosure.

Turning now to FIG. 6, a flow chart depiction of a method 600 of performing a patient pain analysis, in accordance with one embodiment of the present disclosure, is illustrated. The medical device 100 may detect one or more patient body signals (block 610). In one embodiment, detecting at 610 may comprise transmission of one or more body signals recorded by the sensor 130 to the medical device 100. As described above, the medical device 100 may receive various autonomic data, neurological data, endocrine data, metabolic data, tissue stress marker data, etc. Based upon the body signal(s) received, the medical device 100 may determine a patient pain index (block 620). The patient pain index may be a normalized calculation of a patient pain level based upon various objective and/or subjective factors. The objective factors may include a change in one or more indices relating to autonomic, neurological, endocrine, metabolic, and/or tissue stress marker indications in the patient's body. The subjective factors may include an indication from the patient as to the amount and/or quality (e.g., sharp, boring, etc.) of pain being experienced by the patient. The patient pain index may be calculated using various mathematical calculations based upon various weightings attributed to one or more of the factors described above.

A patient pain index may then be compared to a predetermined threshold to determine whether the pain index is at or above the threshold (block 630). The predetermined threshold may be calculated and stored in the medical device 100. In one embodiment, the predetermined threshold may be manually or automatically adjusted based upon one or more factors, such as a change in the patient's health, mood, emotional state, time of day, sleep latency, total sleep time, number and duration of arousals from sleep as well as their time of occurrence, environmental factors, patient activity factors (e.g., exercise versus sleep), the patient's physical fitness index, etc. In an alternative embodiment, one or more patient pain indices may be treated as dynamic values that may be automatically or manually adjusted/weighted (e.g. increased or decreased) based upon the therapy history, (e.g., dose and/or type of medications recently delivered), an increase or decrease in the patient pain tolerance level, adverse therapy effects and safety factors, etc. In some embodiments, a customized pain threshold may be predetermined for a particular patient as a function of the factors listed immediately above or of others. In one embodiment, one or more threshold-based decisions may be changed automatically by the medical device 100, or may be changed based upon input received from an external source (e.g., the patient or a medical professional).

Upon a determination that the patient pain index is below the pain threshold index, the medical device 100 may continue to monitor the patient (block 640) and may continue to detect or receive one or more patient body signals. In one embodiment, the recording, processing and/or analyses of certain patient body signals may only be triggered based upon programmed temporal triggers, detection of one or more changes in body signals, other patient events, etc. For example, processing or analysis of high dimensional, computationally expensive and weak signals such as those generated by the brain cortex, may be undertaken only when changes in the value of certain autonomic or kinetic signals reach or exceed a threshold.

Upon a determination that a patient pain index is above a predetermined threshold, the medical device may further determine if the patient's safety would be compromised by administration of a given drug, or by high dosage of a given drug (block 650).

Development of drug tolerance is common with certain pain medications, requiring increases in dose to attain the same effect as earlier smaller doses. This phenomenon may be detected and quantified by comparing the effects on various autonomic, neurologic and other indices as a function of time. By way of a non-limiting example, changes in pupillary size (e.g., myosis) are caused by opioid analgesics such as morphine. Measurements of pupillary size before and after administration of a compound (when Cmax is reached or at some pre-specified time), are recorded over time for identical doses; if the change ("delta") in pupillary size decrease with the number of administered doses and/or the latency to maximal myosis lengthens, tolerance has occurred and its degree and rate may be then determined. Side effects may be also detected and quantifies (latency to onset, magnitude and duration) using neurologic (e.g., reaction time, attention, posture, coordination, etc.) or autonomic (heart rate, respiratory rate, blood pressure, etc.) among other body signals. Using information from representative patients' samples, changes in normative values in autonomic, neurologic or other systems for a given analgesic compound, dose, route of administration among others are compared to those observed in an individual.

In one embodiment, a body tolerance index associated with the patient is determined. The body tolerance index may be calculated based upon various factors, such as patient weight, height, age, health status, medications provided to patient previously, etc. The body tolerance index may be compared to a baseline reference tolerance index range for the patient chosen from the naïve (e.g., the patient has not been exposed to a medication or to similar medications, or after having been treated). The body tolerance index may refer to the rate and degree to which the patient's response to a medication is lessened or blunted by repeated exposures.

Using changes, if any, in the values of a patient's biological data as a function of repeated exposures to pain medications, a Drug Tolerance Index (DTI) may be calculated as follows:

$$DTI = \Sigma \delta M n(bi)/E + \Sigma \delta L \; n(bi)/E$$

where $\delta M$ is the magnitude of a change, $\delta L$ is latency change, bi is a body index, n(bi) is the number of body indices used in the calculation and E is the number of exposures. E is placed in the denominator since the tolerance decreases with the number of exposures (e.g., it tends towards a "plateau"). DTI may be also calculated using the change in dose required to obtain the same effect (as when the patient received the first or some other dose) with repeated exposures to a medication. The actual doses of medications may be also used. DTI may be a negative or positive integer depending on whether the change or "delta" is deemed positive or negative.

Upon a determination that the patient has developed tolerance to a medication or therapy (this phenomenon may also occur with electrical, thermal or other forms of therapy), the medical device 100 may select or determine the type of medication and the dosage of the selected medication (block 660) or another type of therapy and parameters thereof for delivery to the patient. For example, if the tolerance for medication seems particularly high, the dosage of a particular medication may be increased. An increase or decrease in dosage may be permanent or temporary. Based upon the type and the dosage determination, the medical device 100 may deliver the medication by activating the medication dispenser 340 (block 680).

A Drug Adverse Index (DAI) may be calculated using an approach similar to that described above for DTI using body signals. For example the effect of administering a certain narcotic at a certain dose on heart and respiratory rate, blood pressure, reaction time, etc. and the latency to for example the maximal change in said body signals, may be quantified and used to compute a DAI. In one embodiment of this disclosure, if any change in the values of the DAI is, for example, at least one standard deviation from the mean, an adverse event may be declared, a warning issued and the relevant information logged into memory.

A scale, such as from 0-1 (0 for no subjective effect and 1 for the most severe one) may be applied to quantify adverse effects. This disclosure takes into account that not all adverse effects give rise to symptoms and that monitoring of body indices is necessary to detect them. Hypertension caused by a drug is highly unlikely to be associated with any symptoms and drugs that depress consciousness reduce the patient's ability to feel and/or report symptoms.

In some embodiments, a discomfort level for the patient may be determined. Discomfort herein refers to another manifestation of pain. The discomfort level is defined herein as either (or both) of a lack of stillness or quietness that may be "quantified" by the patient using a numerical or a pictorial scale or objectively, as an index based on the recording and analyses of body signals. Patients that are uncomfortable are fidgety or restless and also have facial expressions and utter sounds (formed or non-formed vocalizations) correlated with the level of discomfort. As a non-limiting example, facial EMG or facial imaging, the recording of formed or non-formed vocalizations or of other sounds (e.g., turning in bed), the recording of the number/unit time (rate), amplitude, velocity, direction of body movements, may be used to compute a discomfort level (the higher its value, the higher the discomfort level). Behavioral evidence of discomfort may manifest before or after a patient complains of pain. A discomfort threshold may be set for each patient at or above which an intervention (e.g., a medication, repositioning of the patient's body, psychological support, etc.) is performed. The discomfort threshold may be based upon various body data and may express the magnitude and/or rate of increase in pain or an absence of pain above a certain level if the index is 0.

Figure 7A:
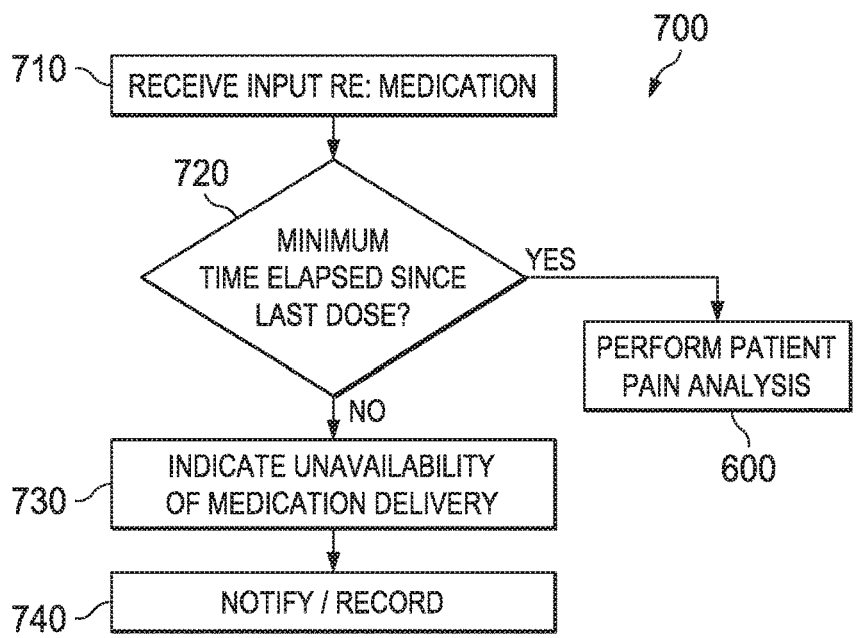
FIG. 7A illustrates a flowchart depiction of the steps for reacting to a medication request from a patient, in accordance with one embodiment of the present disclosure.

Turning now to FIG. 7A, a flowchart depiction of a method 700, an exemplary operation of the medical device 100 following an input from the patient requesting medication, in accordance with one embodiment of the present disclosure, is provided. The patient may send a request for medication to the medical device 100. The medical device 100 may receive the input from the patient regarding the request for medication (block 710). Upon receiving such an input, the medical device 100 may determine whether a minimum time period has elapsed since the delivery of the last dosage (block 720). The minimum time period may be based upon predetermined ranges selected and programmed by a medical professional or may be based on one or more of a safety index, a tolerance index or a pain level. In an alternative embodiment, the predetermined ranges may be adjusted dynamically (e.g., weighted linearly or non-linearly) based on various factors, such as various patient body data levels, pain threshold levels, dosage levels previously administered, discomfort level, time of day, patient's mood, etc.

Upon a determination that the minimum time period has not elapsed since the last dosage, an indication by the medical device 100 may provide an indication of unavailability for medication delivery (block 730). Upon an indication of unavailability of medication, the medical device 100 may notify one or more entities, such as a medical professional, and/or record the event (block 740) or perform a more detailed and extensive analyses of relevant to determine if based on need and safety a therapy may be provided even though the pre-specified time criterion has not been met Upon a determination that minimum time period has indeed elapsed since the last dosage, in response to the input from the patient, the medical device 100 may perform an independent analysis to determine whether or not to automatically deliver pain medication. This analysis may be based upon the detection of body data and the comparison of the pain index to the threshold described in FIG. 6. Therefore, despite the fact that a patient has requested medication, an independent evaluation of the patient's pain being at or above a particular threshold may be made before delivering the patient's medication. Further, automated delivery of pain medication may be performed without input from the patient. In this manner, before the onset of pain, various body data may indicate that pain is impending, and automated delivery of medication may be provided to the patient. In this manner, the onset of pain (or worsening of pain) even may be prevented by the automated delivery of pain medication or of another therapy.

In another embodiment, a decision to automatically withhold or deliver medication may be based, not on time elapsed from the last drug delivery and/or the amount of medication given to a patient, but on body value indices. If a time constraint has been set (e.g., medication is to be delivered every 4 hours) and a patient request medication 2 hours after the last dose, the device may perform analyses of body indices and based on the results assess the safety of drug administration at that time; if deemed safe, the time constraint may be ignored. Adjustments in the dose delivered (lower or higher than programmed) may be automatically performed by the device based on quantification and analyses of body indices correlated with pain level and those indicative of safety of administration.

Figure 7B:
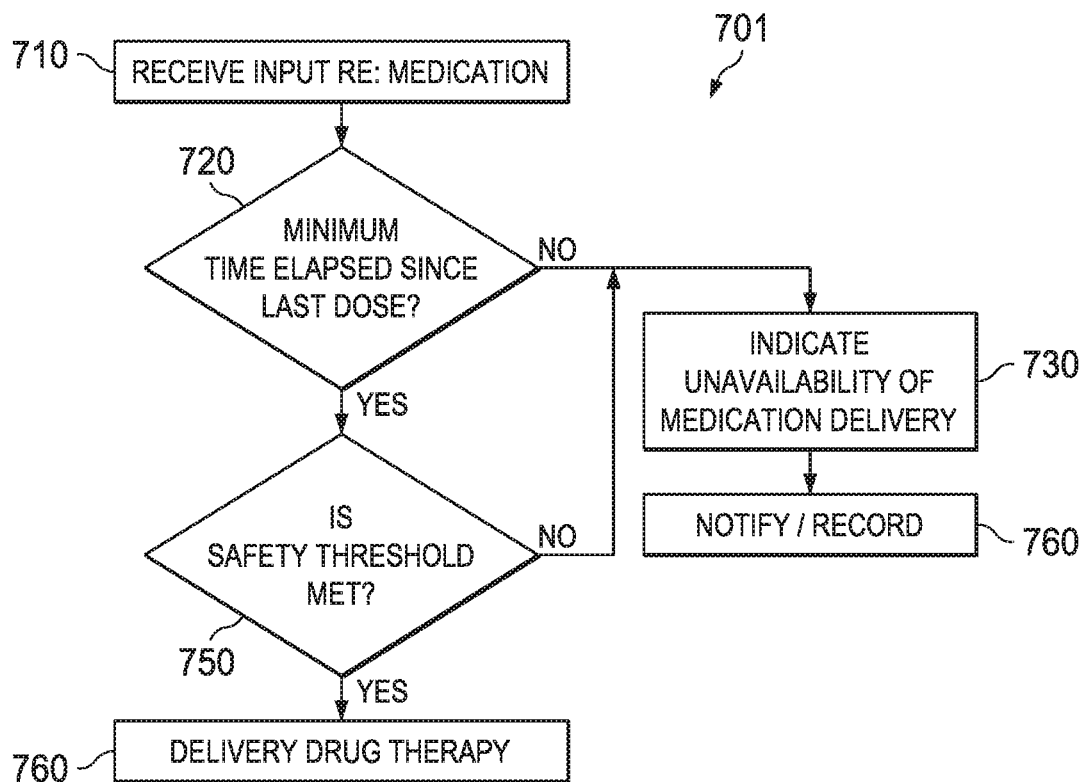
FIG. 7B illustrates a flowchart depiction of the steps for reacting to a medication request from a patient, including a safety determination, in accordance with one embodiment of the present disclosure.

Turning now to FIG. 7B, a flowchart depiction of a method 701, an exemplary operation of the medical device 100 following an input from the patient requesting medication, in accordance with one embodiment of the present disclosure, is provided. Elements 710-740 are generally similar to the like-numbered steps of FIG. 7A and need not be re-discussed.

Upon a determination at 720 that the minimum time period has elapsed since the last dosage, a determination may be made at 750 as to whether drug delivery at the present time would be safe.

The determination at 750 may comprise any of those discussed infra (e.g., responsiveness tests). For example, the responsiveness test may comprise a determination as to whether the patient's responsiveness is above a responsiveness threshold, such as a responsiveness threshold corresponding to the patient having normal responsiveness. More generally, a responsiveness threshold may be set such that a finding by the test that the patient's responsiveness is below it, reflects at least one of a slowing of the patient's reaction time, an increase of the number of incorrect responses given by the patient, an increase in the number and/or magnitude of results indicative of impaired cognition, a state of lethargy from which the patient is easily arousable and will remain awake without further stimulation, a state of patient lethargy from which the patient is arousable but will only remain awake with further stimulation, or a state of patient stupor from which the patient is difficult to arouse or a coma from which the patient is un-arousable.

If the minimum time period has not elapsed, flow may move to blocks 730 and 740. If the minimum time period has elapsed, then drug delivery may be performed (block 760). Therefore, despite the fact that a patient has requested medication, an independent evaluation of the whether drug delivery would be safe may be made before delivering the patient's medication.

Figure 8:
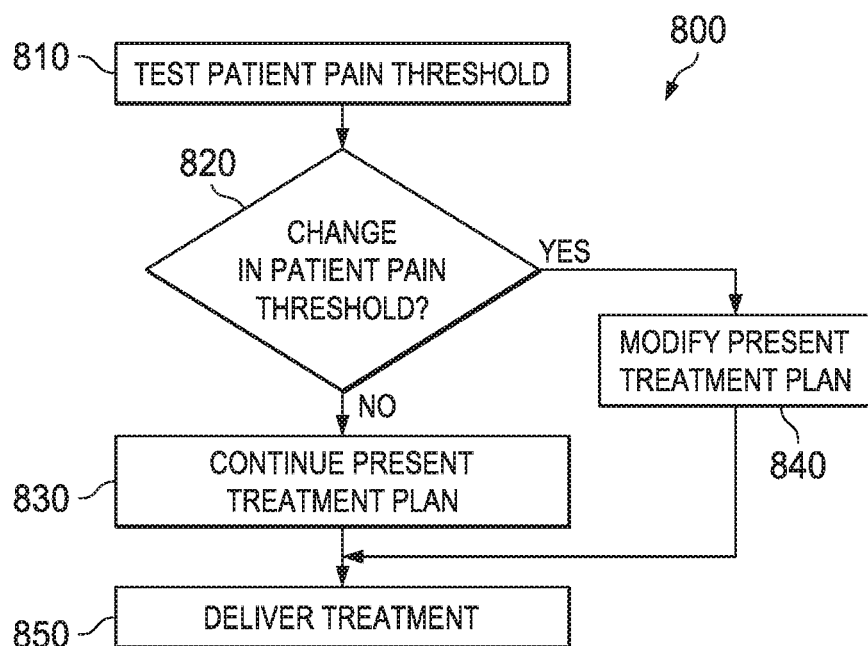
FIG. 8 illustrates a flowchart depiction of the steps for testing a patient pain threshold and taking subsequent action, in accordance with one embodiment of the present disclosure.

Turning to FIG. 8, a flowchart depiction of a method 800 in accordance with one embodiment of the present disclosure is provided. Generally, the method 800 assumes a patient is undergoing a treatment for pain as described herein, and as part of that treatment, a pain threshold of the patient has been previously determined. In the method 800, the patient's pain threshold may be tested at 810 using any appropriate apparatus and/or technique, such as those described elsewhere herein. Generally, noxious stimuli of increasing intensity may be applied to the patient until he or she reports perception of pain. Further, distress and/or suffering thresholds, if desired, may be determined by extrapolation and/or other operations.

A determination may then be made at 820 as to whether the patient's pain threshold has changed, based on the results of the test at 810 and the previous determination of the patient's pain threshold. If the patient's pain threshold has not changed, i.e., is stable, the present treatment plan may be continued at 830 and delivered at 850. If the patient's pain threshold has changed, the present treatment plan may be modified at 840. Modification at block 840 may comprise one or more of changing therapy parameters (increasing a dose or frequency of therapy delivery), switching therapy modality (e.g., from drug delivery to electrical stimulation), or adding a therapy modality (e.g., adding electrical stimulation to ongoing drug delivery). The therapy modified at 840 may then be delivered at 850.

Figure 9:
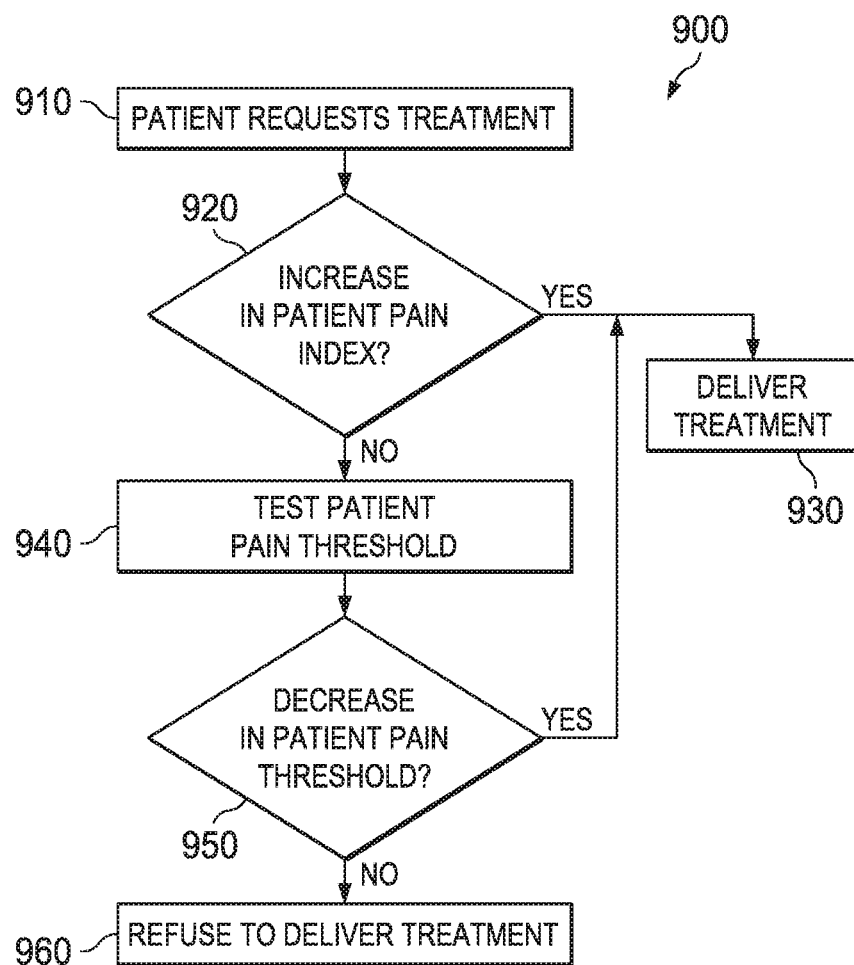
FIG. 9 illustrates a flowchart depiction of the steps for reacting to a medication request from a patient, in accordance with one embodiment of the present disclosure.

Turning to FIG. 9, a flowchart depiction of a method 900 in accordance with one embodiment of the present disclosure is provided. The patient may send a request for medication to the medical device 100 (block 910). Upon receiving such an input, the medical device 100 may determine whether the patient's pain index has increased (block 920). If it has, it may be concluded that the patient's request indicates an increase in his or her pain burden, and the requested treatment may be delivered to the patient (block 930). If it has not, it cannot be determined whether the patient's request is not appropriate in light of his or her pain (i.e., drug-seeking behavior?) or whether the patient's pain threshold has decreased, such that the same pain index value is now relatively higher than formerly. Thus, the patient's pain threshold may be tested (block 940), comparably to that performed at FIG. 8, block 810.

Thereafter, if it is determined at 950 that the patient's pain threshold has decreased, treatment may be delivered at 930. If the patient's pain threshold has not decreased, then the patient may be exhibiting drug-seeking behavior, and the delivery of treatment may be refused at 960.

Figure 10:
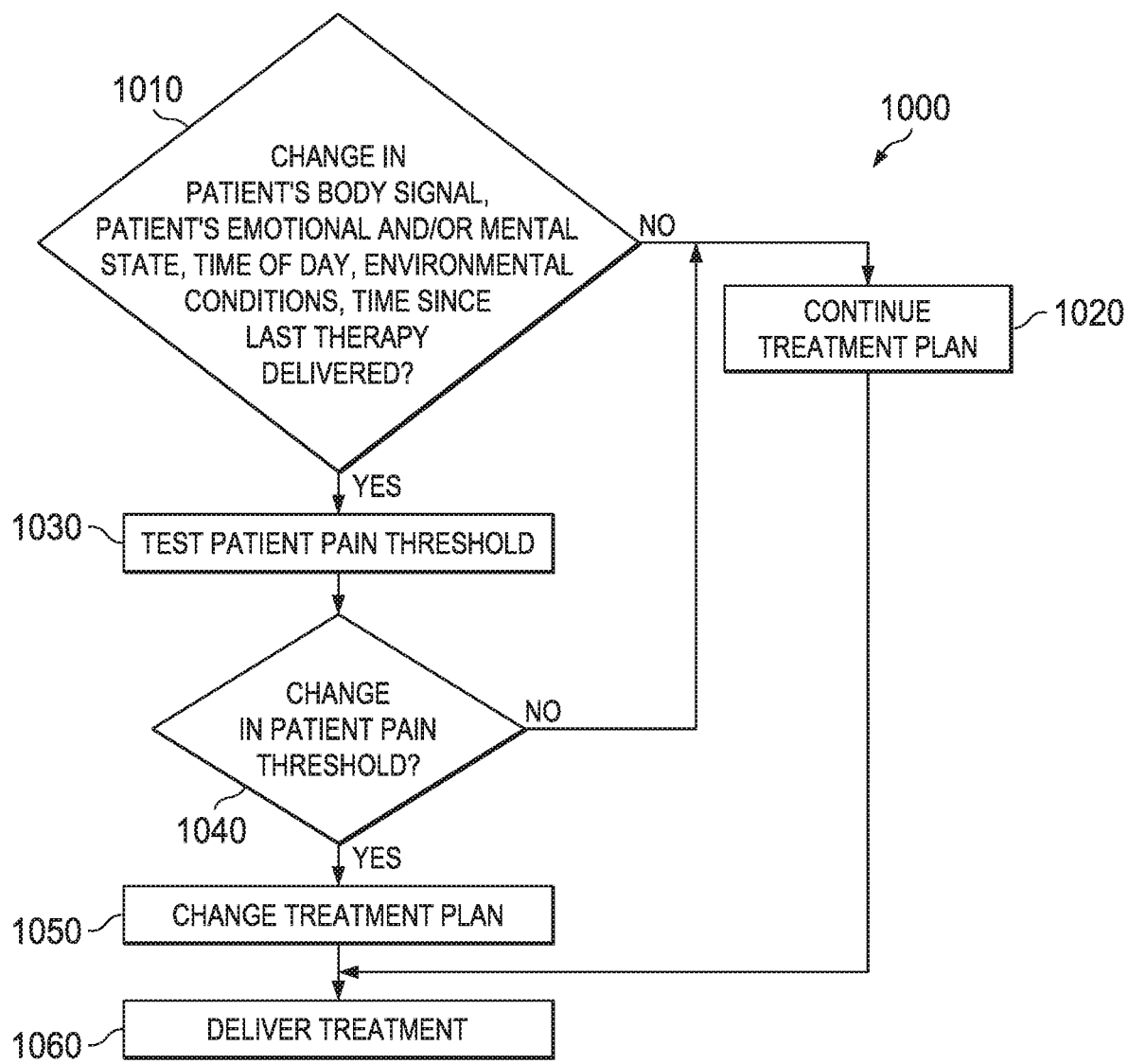
FIG. 10 illustrates a flowchart depiction of the steps for testing a patient pain threshold in response to at least one of a change a body signal, a change in the patient's emotional and/or mental state, time of day, environmental conditions, time elapsed since the last therapy delivery and/or the type of therapy delivered to a patient, in accordance with one embodiment of the present disclosure.

FIG. 10 relates to a method 1000 involving patient pain threshold tests in the context of changes in the patient's emotional and/or mental status, in accordance with one embodiment of the present invention. Specifically, if it is determined at 1010 that the patient's emotional and/or mental status has changed, then the patient's pain threshold may be tested (block 1020), comparably to that performed at FIG. 8, block 810. If the patient pain threshold is determined at 1040 to have changed, then the patient's treatment plan may be changed at 1050. On the other hand, if it were determined at 1010 that no emotional and/or mental status change occurred, then the patient's treatment plan may be continued at 1020. Whether continued at 1020 or changed at 1050, treatment may be delivered at 1060.

Figure 11:
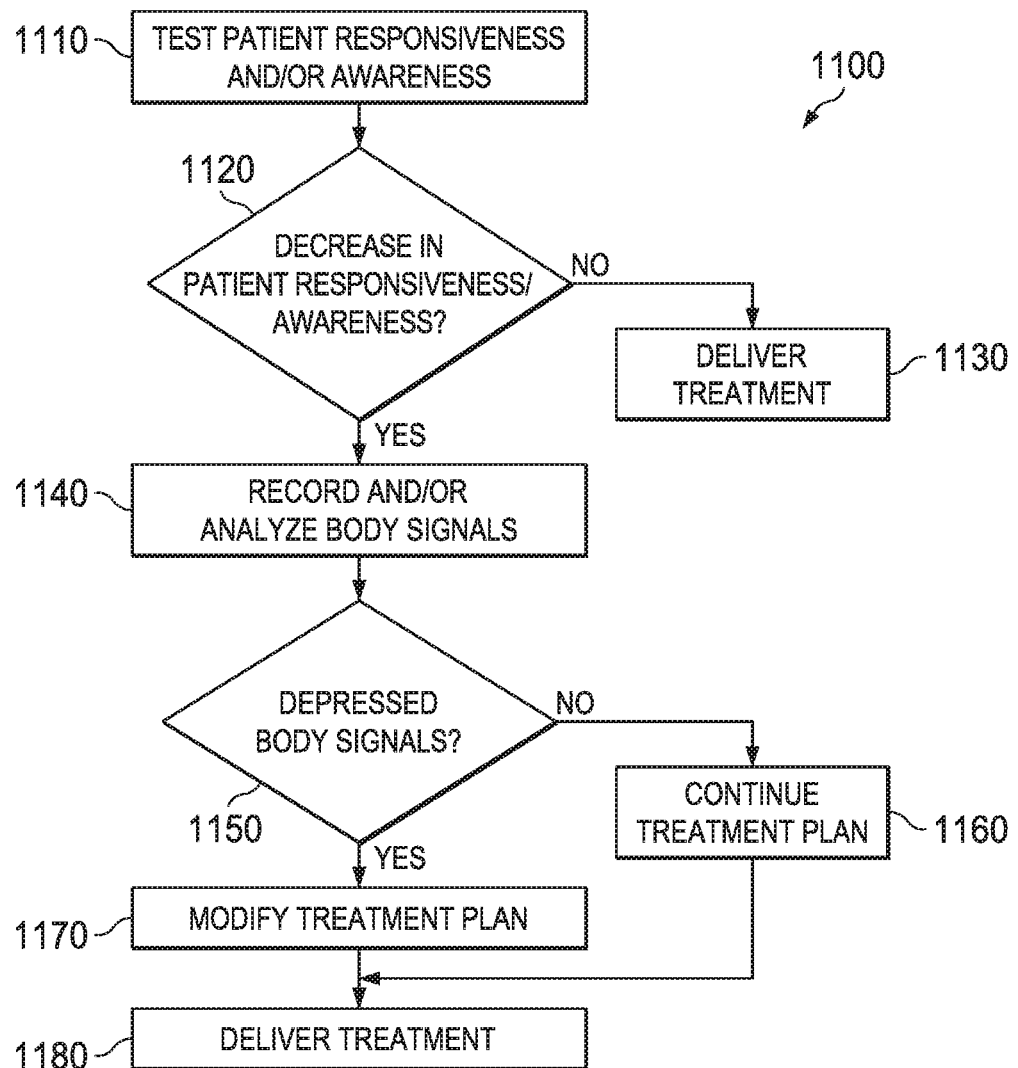
FIG. 11 illustrates a flowchart depiction of the steps for delivering a pain treatment plan in response to a test of a patient's responsiveness and/or awareness, in accordance with one embodiment of the present disclosure.

FIG. 11 provides a flowchart depiction of a method 1100, relating to measures of responsiveness and/or awareness as indicators of safety of administration of CNS depressant drugs and guides for the delivery of treatment for pain. The patient's responsiveness and/or awareness may be tested (block 1110), such as at a time when the medical device 100 is preparing to deliver a pain therapy. More information regarding responsiveness and/or awareness testing may be found in U.S. patent application Ser. No. 12/756,065, filed Mar. 7, 2010, hereby incorporated herein by reference.

If either or both of responsiveness or awareness have not decreased relative to a reference value (the reference may be obtained from a naïve patient (has not received drugs) or at different times after administration of a medication) the current treatment plan may be continued with delivery at 1130. If either or both are determined at 1120 to have decreased, safety of administration of a CNS depressant drug or therapy (e.g., cooling of a brain region) is reassessed. Thus, one or more body signals from the patient may be recorded and/or analyzed at 1140. Exemplary body signals include heart rate, respiratory rate, blood pressure, etc. If one or more body signals are determined at 1150 to be depressed below a certain value, i.e., are indicative of impaired function of the patient's body activity, then his or her treatment plan may be modified (block 1170). If not, his or her treatment plan may be continued at 1160. Whether continued at 1160 or modified at 1170, treatment may then be delivered at 1180. While emphasis on the use of awareness and responsiveness testing has been placed on safety of drug administration, these two signals may be used to estimate pain level and its impact on a patient's ability to function at a certain cognitive level. For example, attention span is susceptible to degradation by pain.

Figure 12:
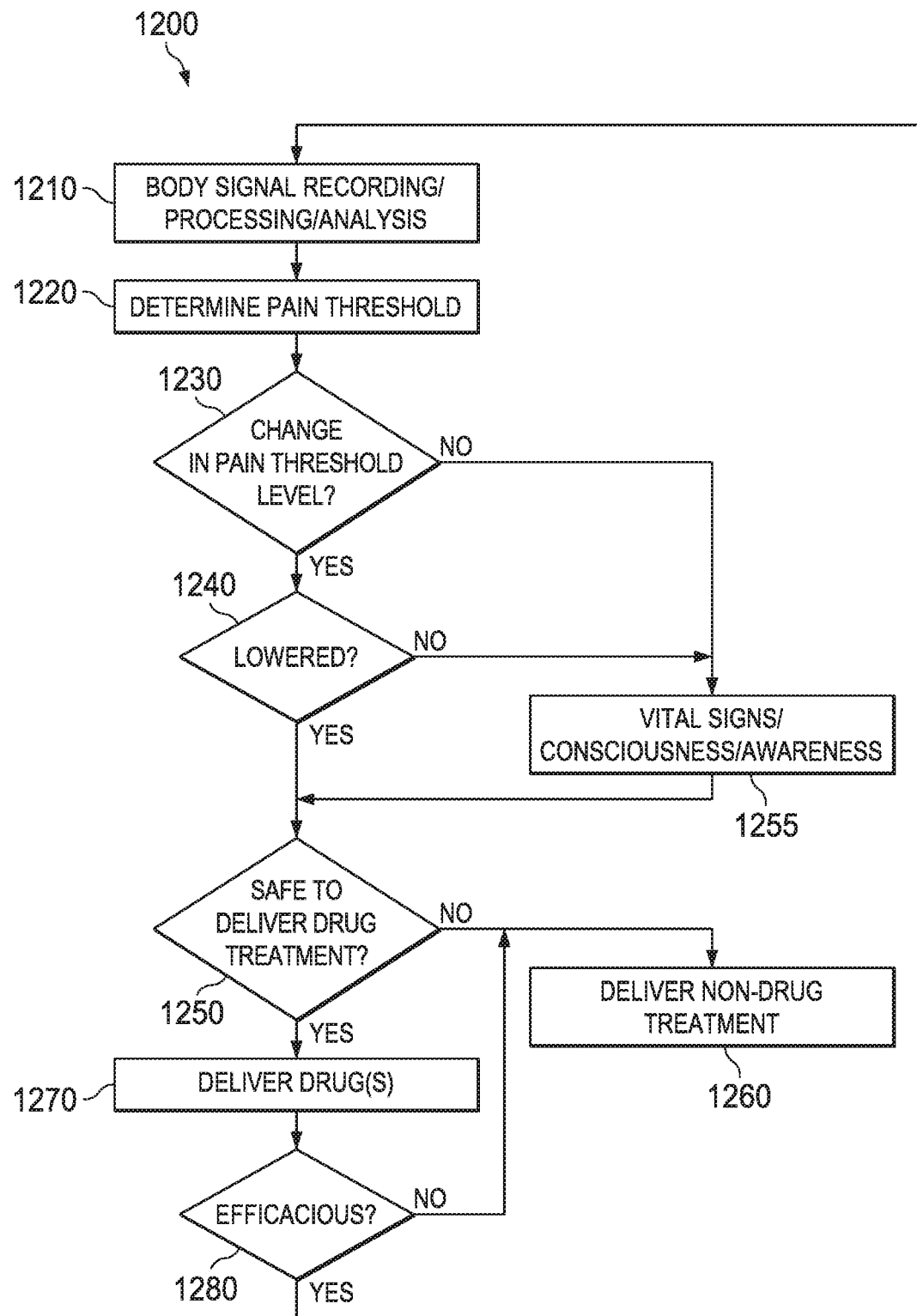
FIG. 12 illustrates a flowchart depiction of the steps for delivering treatments for pain to a patient, in accordance with one embodiment of the present disclosure.

FIG. 12 provides a flowchart depiction of a method 1200 in accordance with one embodiment of the present disclosure. A body signal from a patient may be recorded, processed, and/or analyzed at 1210. In some embodiments, this may be done automatically by a device, in response to receiving at the device a request for delivery of a pain therapy to the patient or in response to a change in a body signal. From the body signal, a pain level may be determined at 1220. The pain level may have changed, as determined at block 1230. If it has lowered (determined at block 1240), it may then be determined at block 1250 whether it is safe to deliver a drug treatment for pain. In some embodiments, the safety determination at 1250 may comprise determining the patient's vital signs, coordination, consciousness, and/or awareness at 1255.

If the safety determination at 1250 reports drug delivery would be unsafe, a non-drug treatment (e.g., an electrical stimulation, etc.) may be delivered at 1260. If the safety determination at 1250 reports drug delivery would be safe, a drug may be delivered at 1270.

After delivery of the drug (block 1270), it may be determined whether drug delivery was efficacious (block 1280), i.e., whether it relieved the patient's pain. If it did, flow may return to block 1210 to begin another iteration of the method 1200. However, if drug delivery was not efficacious, or if it is not safe or convenient to deliver more medications, a non-drug treatment may be delivered at 1260.

After a non-drug treatment may be delivered at 1260, flow may return to block 1210 to begin another iteration of the method 1200.

In some embodiments, the present disclosure may provide a method for providing pain medication, comprising: receiving, at a device, a request for delivery of a pain medication to a patient; receiving, automatically by the device, at least one body data value or a series of values of said patient's body signal(s) in response to the request for delivery of a pain medication; determining a patient pain index based upon the body data series; determining whether the patient pain index is above a reference pain index or pain level; determining a safety index; and allowing, automatically, delivery of a pain medication based on at least one of the safety index or a determination that the patient pain index is above the reference pain index.

In some embodiments of this disclosure, delivery of a therapy may be automatically prompted in response to the value of at least one body index or a change in said value. This prompt may or may not be carried out depending on the safety index.

In some embodiments of this method, allowing delivery of the medication may comprise determining a first dosage of medication received by the patient during a first previous time period; determining whether a second time period has elapsed since the patient received the first dosage, wherein the second time period is based upon the type of medication and first dosage; determining a second dosage of medication (and the type of medication) to deliver to the patient based upon whether or not the second time period has elapsed since the patient received the first dosage and the type of medication the patient had received; and delivering the second dosage of medication to the patient in response to the second time period having elapsed or the type of medication the patient received. Alternatively or in addition, at least one of determining a patient pain index and determining a safety index comprises recording and analyzing at least one body signal to compute a pain index and administering at least one of a patient responsiveness test and/or a patient awareness test and wherein allowing delivery of a pain medication is based on a determination that the patient pain index is above the reference pain index and a determination that the patient's responsiveness exceeds a responsiveness safety threshold. In some embodiments, the safety index may be based on neurological signals other than responsiveness and/or awareness or on autonomic, metabolic, endocrine, or tissue-stress marker signals.

This method may further comprise automatically implementing or changing a delivery of a pain medication if at least one of a pain level is above a certain reference value, a pain threshold is below a certain reference value, a body tolerance is above a certain reference value, an emotional state is negative, or the pain index is above a reference value.

In another embodiment, the present disclosure provides a method for providing pain medication to a patient, comprising receiving automatically, at least a first body data value or series of values of a patient; determining a first discomfort index of the patient based upon the first body data value or series; determining whether the first discomfort index exceeds a first discomfort index threshold; and providing a first therapy in response to determining that the first discomfort index exceeds the first comfort index threshold.

This method for providing pain medication may further comprise receiving a second body data value or series of values of the patient; determining a second discomfort index of the patient based upon the second body data value or series of values; determining whether the second discomfort index exceeds a second discomfort index threshold; determining a second therapy in response to determining that the second discomfort index does exceed the second discomfort index threshold; and providing the second therapy to the patient.

In another embodiment, the present disclosure provides a method, comprising receiving at a device, a request for delivery of a pain therapy to a patient; receiving, automatically by the device, at least one body data value or series of values in response to the request for delivery of a pain therapy; determining a patient pain index based upon the body data value or series or values; determining whether the patient pain index is above a patient pain index threshold; and automatically delivering a pain therapy to the patient in response to determining that the patient pain index is above the patient pain index threshold. This method may further comprise administering a responsiveness test to the patient, wherein automatically delivering a pain therapy comprises delivering a pain therapy in response to determining that the patient pain index is above the patient pain index threshold and determining that the patient's responsiveness exceeds a responsiveness threshold.

In another embodiment, the present disclosure provides a method for providing pain medication, comprising receiving at least one of a request for delivery of a pain medication from a patient, an indication of an elapsed time period, or a request for administration of a responsiveness test to a patient; administering a responsiveness test to the patient in response to the receiving; and allowing delivery of a pain medication based on a determination that the patient's responsiveness is above a certain responsiveness threshold. In this method, the determination that the patient's responsiveness is above the responsiveness threshold may correspond to the patient having normal responsiveness.

Alternatively or in addition, this method may further comprise receiving at least one body data value or series of values of the patient in response to a determination that the patient's responsiveness is not above the responsiveness threshold; determining at least one of heart rate, respiration rate, blood pressure, and oxygen saturation based on the at least one body data value or series of values; determining whether the at least one heart rate, respiration rate, blood pressure or oxygen saturation is below a reference heart rate threshold, respiration rate threshold, blood pressure threshold, or oxygen saturation threshold; and allowing delivery of a pain medication based on a determination that the at least one of a heart rate, respiration rate, blood pressure or oxygen saturation is above said reference heart rate threshold, respiration rate threshold, blood pressure threshold, or oxygen saturation threshold. This method may further comprise performing an action selected from suspending a treatment plan and modifying a treatment plan based on a determination that the at least one of a heart rate, respiration rate, blood pressure or oxygen saturation is below a reference heart rate threshold, respiration rate threshold, blood pressure threshold, or oxygen saturation threshold.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below.

In some embodiments, the present disclosure may relate to one or more of the following numbered paragraphs.

101. A method for pain prophylaxis or prevention comprising at least one of:
determining a pain threshold and comparing said threshold to a pain threshold reference value;
determining a body tolerance index and comparing said body tolerance index to a body tolerance index reference value;
determining a pain index and comparing said pain index to a pain index reference value;
determining a safety index and comparing said safety index to a safety index reference value;
determining an emotional state of the patient and comparing it to a positive emotional state reference value; and
automatically delivering a pain treatment regimen if at least one of:
the pain threshold is below the pain threshold reference value;
the body tolerance index is above the body tolerance index reference value;
the pain index is above the pain index reference value;
the safety index is above the safety index reference value; and
the emotional state is below said positive emotional state reference value.

201. A medical device system for providing medication to a patient, the medical device comprising:
a first receiver for receiving at least one body signal from a patient;
a controller operatively coupled to said receiver, said controller adapted to:
determine a patient pain index based at least in part on said at least one body signal;
compare said patient pain index to a first reference value; and
determine at least one treatment parameter based upon comparing said pain index to a reference value; and
a therapy unit to cause an application of a medication in response to said comparing of said pain index being outside said reference value.

202. The medical device system of numbered paragraph 201, wherein said body signal comprises at least one of heart beat data, blood pressure data, respiration data, blood gas data, neurological data, endocrine data, metabolic data, or tissue stress marker data.

203. The medical device system of numbered paragraph 201, wherein said medical device further comprises:
a reservoir to store at least one medication;
a medication dispenser operatively coupled to said reservoir, said medication dispenser adapted to extract medication from said reservoir;
a body data collection module adapted for receiving said at least one body signal;
a patient pain module to determine a patient pain index based least partially upon said body signal; and
a controller adapted to control at least one operation of said medication dispenser based upon said patient pain module.

204. The medical device system of numbered paragraph 203, wherein said medication dispenser is a pumping device that is capable of pumping medication from the reservoir to the patient.

205. The medical device system of numbered paragraph 205, wherein at least one of a different medication or a different pain treatment regimen are delivered to the patient if the safety index is below the safety index reference value and one of:
the pain threshold has decreased since the administration of a first pain treatment regimen;
body tolerance has developed since the administration of a first pain treatment regimen;
the pain index is above the pain index reference value;
the patient's emotional state is negative.

206. The medical device system of numbered paragraph 205, wherein a non-pharmacological treatment is delivered if at least one of the pain threshold is below the pain threshold reference value, the body tolerance index is above the body tolerance index reference value, the pain index is above the pain index reference value, the patient's emotional state is negative, or the safety index is indicative of high risk of adverse events.

301. A non-transitory computer readable program storage unit encoded with instructions that, when executed by a computer, perform a method, comprising:
receiving, automatically at the device, at least one body data series;
determining a patient pain index based upon said body data series;
determining whether the patient pain index is above a patient pain index reference value;
automatically delivering a pain therapy to the patient in response to determining that said patient pain index is above said patient pain index reference value.

401. A medical device system for providing medication to a patient, the medical device comprising:
a first receiver for receiving at least one body signal from a patient;
a controller operatively coupled to said receiver, said controller adapted to:
determine a patient pain index based at least in part on said at least one body signal;
determine if said patient pain index is commensurate with the patient's subjective pain level
determine at least one treatment parameter based upon comparing said pain index being commensurate with said patient's subjective pain level; and
a therapy unit to cause an application of a medication in response to said determination that the pain index is commensurate with the patient's subjective pain level.

501. A medical device system for providing medication to a patient, the medical device comprising:
a first receiver for receiving at least one body signal from a patient;
a controller operatively coupled to said receiver, said controller adapted to:
determine a patient pain index based at least in part on said at least one body signal;
determine if said patient pain index is commensurate with the patient's subjective pain level
a therapy unit to withhold an application of a medication in response to said determination that the pain index is not commensurate with the patient's subjective pain level.

What is claimed is:

1. A medical device system, comprising:
a sensor that is a pupil dilation sensor operable to measure an amount of dilation of a pupil of a patient's eye;
a patient pain module configured to determine a patient pain index based at least in part upon increases in pupillary size measured by the sensor; and
a controller configured to deliver a therapy to the patient based upon at least the patient pain index crossing a first pain index threshold as determined from the increase in pupillary size.

2. The medical device system of claim 1, wherein the therapy is at least one of a medication, an electrical stimulation and a thermal therapy.

3. The medical device system of claim 1, wherein the magnitude of increase in pupillary size determines at least one of: the dose of a medication, the intensity of electrical stimulation, the intensity of thermal energy, and the duration of the delivery of the therapy.

4. The medical device system of claim 1, wherein the medical device is capable of determining a rate of change in pupillary size.

5. The medical device system of claim 1, wherein the therapy is a medication, and wherein the medical device is further configured to determine a change in pupillary size in response to the release of the medication, the change in pupillary size being measured by the pupil dilation sensor.

6. The medical device system of claim 5, wherein the medical device is further configured to determine a change in a future dose of the medication based at least on a measured amount of pupillary constriction in response to the release of the medication.

7. The medical device system of claim 5, wherein the medical device is further configured to determine a drug tolerance index based at least on a measured amount of pupil size change in response to the release of the medication.

8. A medical device system, comprising:
at least two sensors comprising a pupil dilation sensor operable to measure changes in pupillary size of a pupil of a patient's eye and an autonomic sensor operable to measure at least one autonomic body signal from the autonomic system of the patient;
a patient pain module configured to determine a patient pain index based at least in part upon the measurements from the at least two sensors; and
a controller configured to control delivery of a therapy to the patient based upon at least the patient pain index crossing a first pain index threshold.

9. The medical device system of claim 8, wherein the therapy is at least one of a medication, an electrical stimulation and a thermal therapy.

10. The medical device system of claim 8, wherein the first pain index threshold is indicative of a level of pain below a pain perception threshold.

11. The medical device system of claim 8, wherein the determination that the patient pain index is above the first pain index threshold is based on a change of pupillary size.

12. The medical device system of claim 8, wherein the at least one autonomic body signal comprises at least one of a: heart rate, heart rate variability, blood pressure, blood pressure variability, skin resistance, skin resistance variability, respiratory rate, respiratory rate variability, oxygen saturation, and oxygen saturation variability.

13. The medical device system of claim 8, wherein the patient pain index is further based on at least one of a: gastric motility, gastric motility variability, motor activity, motor activity variability, rate and loudness of formed and non-formed vocalizations, and variability of rate and loudness of formed and non-formed vocalizations.

14. The medical device system of claim 8, wherein the measurements from the pupil dilation sensor comprises at least one of a: pupillary size; speed of change of pupillary size; frequency of changes in pupillary size per unit time; pupillary shape; and speed, magnitude and frequency of pupillary size changes in response to light, darkness, noxious stimuli, emotional stimuli, cognitive stimuli, and administration of a treatment regimen.

15. A medical device system, comprising:
at least one sensor comprising at least one of a pupil dilation sensor operable to measure changes in pupillary size of a pupil of a patient's eye and an autonomic sensor operable to measure at least one autonomic body signal from the autonomic system of the patient;
a patient pain module configured to determine a patient pain index based at least in part upon increases in pupillary size; and
a controller configured to control delivery of a therapy to the patient based upon at least the patient pain index crossing a first pain index threshold.

16. The medical device system of claim 15, wherein the therapy is at least one of a medication, an electrical stimulation and a thermal therapy.

17. The medical device system of claim 15, wherein the at least one autonomic body signal comprises at least one of a: heart rate, heart rate variability, blood pressure, blood pressure variability, skin resistance, skin resistance variability, respiratory rate, respiratory rate variability, oxygen saturation, and oxygen saturation variability.

18. The medical device system of claim 15, wherein the patient pain index is further based on at least one of a: gastric motility, gastric motility variability, motor activity, motor activity variability, rate and loudness of formed and non-formed vocalizations, and variability of rate and loudness of formed and non-formed vocalizations.

19. The medical device system of claim 15, wherein the measurements from the pupil dilation sensor comprises at least one of a: pupillary size; speed of change of pupillary size; frequency of changes in pupillary size per unit time; pupillary shape; and speed, magnitude and frequency of pupillary size changes in response to light, darkness, noxious stimuli, emotional stimuli, cognitive stimuli, or administration of a treatment regimen.

20. The medical device system of claim 15, wherein the therapy is a medication, and wherein the medical device is further configured to determine a change in pupillary size in response to the release of the medication, the change in pupillary size being measured by the pupil sensor.

* * * * *